US012576144B2

(12) United States Patent
Muthumani et al.

(10) Patent No.: US 12,576,144 B2
(45) Date of Patent: Mar. 17, 2026

(54) VACCINES AGAINST POWASSAN VIRUS, AND METHODS OF USING SAME

(71) Applicant: THE WISTAR INSTITUTE OF ANATOMY AND BIOLOGY, Philadelphia, PA (US)

(72) Inventors: Kar Muthumani, Cherry Hill, NJ (US); David Weiner, Merion, PA (US); Hyeree Choi, Philadelphia, PA (US); Sagar B. Kudchodkar, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 1105 days.

(21) Appl. No.: 17/416,199

(22) PCT Filed: Dec. 20, 2019

(86) PCT No.: PCT/US2019/067798
    § 371 (c)(1),
    (2) Date: Jun. 18, 2021

(87) PCT Pub. No.: WO2020/132418
    PCT Pub. Date: Jun. 25, 2020

(65) Prior Publication Data
    US 2022/0054620 A1     Feb. 24, 2022

Related U.S. Application Data

(60) Provisional application No. 62/782,407, filed on Dec. 20, 2018, provisional application No. 62/885,405, filed on Aug. 12, 2019.

(51) Int. Cl.
    *A61K 39/12*     (2006.01)
    *C12N 7/00*      (2006.01)
    *A61K 39/00*     (2006.01)

(52) U.S. Cl.
    CPC ................ *A61K 39/12* (2013.01); *C12N 7/00* (2013.01); *A61K 2039/53* (2013.01); *C12N 2770/24134* (2013.01)

(58) Field of Classification Search
    None
    See application file for complete search history.

(56) References Cited

U.S. PATENT DOCUMENTS

| | | |
|---|---|---|
| 6,962,708 B1 | 11/2005 | Chambers |
| 2005/0163804 A1* | 7/2005 | Chang ................ C07K 16/1081 435/235.1 |
| 2007/0166329 A1 | 7/2007 | Chang |

FOREIGN PATENT DOCUMENTS

| | | | |
|---|---|---|---|
| WO | WO 2016/022958 | * | 11/2016 |
| WO | 2017223491 | | 12/2017 |

OTHER PUBLICATIONS

Alignment of SEQ 1 with Geneseq db access No. BCM04964 2016.*
Alignment with SEQ 2 with UniProt db access No. E2I7G8_9FLAV 2010.*

(Continued)

*Primary Examiner* — Shanon A. Foley
(74) *Attorney, Agent, or Firm* — Riverside Law LLP

(57) ABSTRACT

An aspect of the present invention is related to nucleic acid constructs capable of expressing at least one Powassan virus (POWV) antigen that elicits an immune response in a mammal against POWV virus, and methods of use thereof.

16 Claims, 15 Drawing Sheets
Specification includes a Sequence Listing.

(56)                    References Cited

OTHER PUBLICATIONS

Alignment with SEQ 5 with GenEmbl db access No. HM440563 2010.*

Alignment of SEQ 6 with Geneseq db access No. BCM04965 in WO2016022958 2016.*

Alignment with SEQ 9 with GenEmbl db access No. HM440563 2010.*

Alignment with SEQ 10 with UniProt db access No. E2I7G8_9FLAV 2010.*

Beasley et al. (Virus Research. 201; 79: 81-89).*

VanBlargen et al. (Cell Reports. Dec. 18, 2018; 25: 3382-3392).*

Pending_Patents database PCTUS1544284 (application No. of: WO 2016/022958) SEQ ID No. 2 alignment with instant SEQ ID No. 2—2015.*

Pending Patents AA db PCT-US15-44284 (application No. of: WO 2016/022958) SEQ ID No. 2 alignment with instant SEQ ID No. 8—2015.*

Geneseq db access No. BCM04965 in WO2016022958 Lipkin with instant SEQ ID No. 10—2016.*

Published Applications db SEQ 20 alignment in US20050163804 with instant SEQ 6; Jul. 2005.*

International Search Report and Written Opinion issued in App. No. PCT/US2019/067798, mailing date Mar. 20, 2020, 11 pages.

Vanblargan et al., "An mRNA Vaccine Protects Mice against Multiple Tick-Transmitted Flavivirus Infections", Cell Reports, (Dec. 18, 2018), vol. 25, No. 12, pp. 3382-3392, XP055721406.

* cited by examiner

Week 0            Week 2                    Week 3

Immunization      Immunization              Collect sera and
1 + EP           #2 + EP                   Splenocytes Group (n=4)

1)  POWV-Env-25 ug
2)  POWV-Cap-25 ug
3)  POWV-Cap+Env (25ug)
4)  pMV101-25 ug

POWV-SEV or pMV101 vector
Injection (25ug)

Days 0          14          21

POWV vaccine- mouse

POWV conv sera- human

VACCINES AGAINST POWASSAN VIRUS, AND METHODS OF USING SAME

CROSS REFERENCE TO RELATED APPLICATIONS

This application is the U.S. national phase application filed under 35 U.S.C. § 371 claiming benefit of International Patent Application No. PCT/US2019/067798, filed on Dec. 20, 2019, which is entitled to priority of U.S. Provisional Application No. 62/782,407, filed Dec. 20, 2018, and U.S. Provisional Application No. 62/885,405, filed Aug. 12, 2019, each of which is hereby incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206193-0022-00US Sequence Listing.txt" in ASCII format. The text file containing the Sequence Listing of the present application was created on Jun. 18, 2021 and is 32,823 bytes in size.

FIELD OF THE INVENTION

The present invention relates to a recombinant nucleotide sequence that encodes a Powassan viral antigen, and functional fragments thereof. The invention also relates to a combination of multiple recombinant nucleotide sequences encoding Powassan viral antigens for generating immunity against Powassan virus disease. The compositions of the invention provide improved methods for inducing immune responses, and for prophylactically and/or therapeutically immunizing individuals against Powassan virus.

BACKGROUND OF THE INVENTION

Powassan virus (POWV) is a rare tick-borne member of the family Flaviviridae, first reported in 1958. It is the only tick-borne member of the genus Flavivirus with human pathogenicity in North America. Small and medium-sized mammals are common reservoirs (notably, woodchucks and white-footed mice, and several species of tick act as vectors. Pathogenesis is due to lymphocytic infiltration of perivascular neuronal tissue with a predilection for gray matter, including thalamus, midbrain, and cerebellum.

POWV incidence is under-reported with only the most severe encephalitis cases reported. Approximately 10% of the reported central nervous system (CNS) infections have been fatal, and an additional 50% have produced long-term neurologic sequelae, including hemiplegia and headaches. Transmission from tick to host is within 15 minutes or less. 7-14 days after tick bite an infected individual will exhibit symptoms such as flu like symptoms, fever, headache, nausea, vomiting muscle weakness, and stiff neck. Patients with POWV infection typically exhibit encephalitis after an incubation period of 1-4 weeks. Other long-term symptoms include meningitis, paralysis, speech difficulties, and fatigue. In addition, there is a greater risk of endemic of POWV than Lyme.

Therefore, there remains a need to develop a vaccine for prophylaxis against POWV. The present invention addresses this need.

BRIEF SUMMARY OF THE INVENTION

In one embodiment, the invention relates to an immunogenic composition comprising a nucleic acid molecule encoding at least one consensus Powassan virus (POWV) antigen. In one embodiment, the POWV antigen is a pre-membrane-envelope (prME) antigen, a capsid antigen, or a combination thereof.

In one embodiment, the nucleic acid molecule encodes a peptide comprising an amino acid sequence having at least about 90% identity over an entire length of the amino acid sequence of SEQ ID NO: 2, SEQ ID NO: 6 or SEQ ID NO: 10. In one embodiment, the nucleic acid molecule encodes a peptide comprising an immunogenic fragment comprising at least about 90% identity over at least 60% of the amino acid sequence of SEQ ID NO: 2, SEQ ID NO: 6 or SEQ ID NO:10. In one embodiment, the nucleic acid molecule encodes a peptide comprising the amino acid sequence of SEQ ID NO: 2, SEQ ID NO: 6 or SEQ ID NO: 10. In one embodiment, the nucleic acid molecule encodes a peptide comprising an immunogenic fragment comprising at least 60% of the amino acid sequence of SEQ ID NO: 2, SEQ ID NO: 6 or SEQ ID NO: 10.

In one embodiment, the nucleic acid molecule is a DNA molecule or an RNA molecule.

In one embodiment, the nucleic acid molecule comprises a nucleotide sequence having at least about 90% identity over an entire length of a nucleotide sequence of SEQ ID NO: 1, SEQ ID NO: 5 or SEQ ID NO: 9. In one embodiment, the nucleic acid molecule comprises an immunogenic fragment of a nucleotide sequence having at least about 90% identity over at least 60% of the nucleotide sequence of SEQ ID NO: 1. SEQ ID NO: 5 or SEQ ID NO: 9. In one embodiment, the nucleic acid molecule comprises a nucleotide sequence of SEQ ID NO: 1, SEQ ID NO: 5 or SEQ ID NO: 9. In one embodiment, the nucleic acid molecule comprises an immunogenic fragment comprising at least 60% of the nucleotide sequence of SEQ ID NO: 1. SEQ ID NO: 5 or SEQ ID NO: 9.

In one embodiment, the nucleotide sequence encoding the peptide is operably linked to at least one regulatory sequence. In one embodiment, at least one regulatory sequence is a start codon, an IgE leader sequence or a stop codon.

In one embodiment, the nucleic acid molecule encodes a peptide comprising an amino acid sequence having at least about 90% identity over an entire length of the amino acid sequence of SEQ ID NO: 2, SEQ ID NO: 6 or SEQ ID NO: 10, operably linked to an amino acid sequence as set forth in SEQ ID NO: 13. In one embodiment, the nucleic acid molecule encodes an immunogenic fragment comprising at least about 90% identity over at least 60% of the amino acid sequence of SEQ ID NO: 2, SEQ ID NO: 6 or SEQ ID NO: 10, operably linked to an amino acid sequence as set forth in SEQ ID NO: 13. In one embodiment, the nucleic acid molecule encodes the amino acid sequence of SEQ ID NO: 2, SEQ ID NO: 6 or SEQ ID NO: 10, operably linked to an amino acid sequence as set forth in SEQ ID NO: 13. In one embodiment, the nucleic acid molecule encodes an immunogenic fragment comprising at least 60% of the amino acid sequence of SEQ ID NO: 2, SEQ ID NO: 6 or SEQ ID NO: 10, operably linked to an amino acid sequence as set forth in SEQ ID NO: 13.

In one embodiment, the nucleic acid molecule comprises a nucleotide sequence having at least about 90% identity over an entire length of a nucleotide sequence of SEQ ID NO: 1, SEQ ID NO: 5 or SEQ ID NO: 9, operably linked to an nucleotide sequence encoding SEQ ID NO: 13. In one embodiment, the nucleic acid molecule comprises an immunogenic fragment of a nucleotide sequence having at least about 90% identity over at least 60% of the nucleotide sequence of SEQ ID NO: 1, SEQ ID NO: 5 or SEQ ID NO: 9, operably linked to an nucleotide sequence encoding SEQ ID NO: 13. In one embodiment, the nucleic acid molecule comprises a nucleotide sequence of SEQ ID NO: 1, SEQ ID NO: 5 or SEQ ID NO: 9, operably linked to an nucleotide sequence encoding SEQ ID NO: 13. In one embodiment, the nucleic acid molecule comprises an immunogenic fragment of a nucleotide sequence of SEQ ID NO: 1, SEQ ID NO: 5 or SEQ ID NO: 9, operably linked to an nucleotide sequence encoding SEQ ID NO: 13.

In one embodiment, the nucleic acid molecule comprises an expression vector.

In one embodiment, the nucleic acid molecule is incorporated into a viral particle.

In one embodiment, the immunogenic composition further comprises a pharmaceutically acceptable excipient.

In one embodiment, the immunogenic composition further comprises an adjuvant.

In one embodiment, the invention relates to a nucleic acid molecule encoding at least one consensus Powassan virus (POWV) antigen. In one embodiment, the POWV antigen is a prME antigen, a capsid antigen, or a combination thereof.

In one embodiment, the nucleic acid molecule encodes a peptide comprising an amino acid sequence having at least about 90% identity over an entire length of the amino acid sequence of SEQ ID NO: 2, SEQ ID NO: 6 or SEQ ID NO: 10. In one embodiment, the nucleic acid molecule encodes a peptide comprising an immunogenic fragment comprising at least about 90% identity over at least 60% of the amino acid sequence of SEQ ID NO: 2, SEQ ID NO: 6 or SEQ ID NO:10. In one embodiment, the nucleic acid molecule encodes a peptide comprising the amino acid sequence of SEQ ID NO: 2, SEQ ID NO: 6 or SEQ ID NO: 10. In one embodiment, the nucleic acid molecule encodes a peptide comprising an immunogenic fragment comprising at least 60% of the amino acid sequence of SEQ ID NO: 2, SEQ ID NO: 6 or SEQ ID NO: 10.

In one embodiment, the nucleic acid molecule is a DNA molecule or an RNA molecule.

In one embodiment, the nucleic acid molecule comprises a nucleotide sequence having at least about 90% identity over an entire length of a nucleotide sequence of SEQ ID NO: 1, SEQ ID NO: 5 or SEQ ID NO: 9. In one embodiment, the nucleic acid molecule comprises an immunogenic fragment of a nucleotide sequence having at least about 90% identity over at least 60% of the nucleotide sequence of SEQ ID NO: 1. SEQ ID NO: 5 or SEQ ID NO: 9. In one embodiment, the nucleic acid molecule comprises a nucleotide sequence of SEQ ID NO: 1, SEQ ID NO: 5 or SEQ ID NO: 9. In one embodiment, the nucleic acid molecule comprises an immunogenic fragment comprising at least 60% of the nucleotide sequence of SEQ ID NO: 1, SEQ ID NO: 5 or SEQ ID NO: 9.

In one embodiment, the nucleotide sequence encoding the peptide is operably linked to at least one regulatory sequence. In one embodiment, at least one regulatory sequence is a start codon, an IgE leader sequence or a stop codon.

In one embodiment, the nucleic acid molecule encodes a peptide comprising an amino acid sequence having at least about 90% identity over an entire length of the amino acid sequence of SEQ ID NO: 2, SEQ ID NO: 6 or SEQ ID NO: 10, operably linked to an amino acid sequence as set forth in SEQ ID NO: 13. In one embodiment, the nucleic acid molecule encodes an immunogenic fragment comprising at least about 90% identity over at least 60% of the amino acid sequence of SEQ ID NO: 2, SEQ ID NO: 6 or SEQ ID NO: 10, operably linked to an amino acid sequence as set forth in SEQ ID NO: 13. In one embodiment, the nucleic acid molecule encodes the amino acid sequence of SEQ ID NO: 2, SEQ ID NO: 6 or SEQ ID NO: 10, operably linked to an amino acid sequence as set forth in SEQ ID NO: 13. In one embodiment, the nucleic acid molecule encodes an immunogenic fragment comprising at least 60% of the amino acid sequence of SEQ ID NO: 2, SEQ ID NO: 6 or SEQ ID NO: 10, operably linked to an amino acid sequence as set forth in SEQ ID NO: 13.

In one embodiment, the nucleic acid molecule comprises a nucleotide sequence having at least about 90% identity over an entire length of a nucleotide sequence of SEQ ID NO: 1, SEQ ID NO: 5 or SEQ ID NO: 9, operably linked to an nucleotide sequence encoding SEQ ID NO: 13. In one embodiment, the nucleic acid molecule comprises an immunogenic fragment of a nucleotide sequence having at least about 90% identity over at least 60% of the nucleotide sequence of SEQ ID NO: 1, SEQ ID NO: 5 or SEQ ID NO: 9, operably linked to an nucleotide sequence encoding SEQ ID NO: 13. In one embodiment, the nucleic acid molecule comprises a nucleotide sequence of SEQ ID NO: 1, SEQ ID NO: 5 or SEQ ID NO: 9, operably linked to an nucleotide sequence encoding SEQ ID NO: 13. In one embodiment, the nucleic acid molecule comprises an immunogenic fragment of a nucleotide sequence of SEQ ID NO: 1, SEQ ID NO: 5 or SEQ ID NO: 9, operably linked to an nucleotide sequence encoding SEQ ID NO: 13.

In one embodiment, the nucleic acid molecule comprises an expression vector.

In one embodiment, the nucleic acid molecule is incorporated into a viral particle.

In one embodiment, the invention relates to consensus Powassan virus (POWV) antigens. In one embodiment, the POWV antigen is a prME antigen, a capsid antigen, or a combination thereof. In one embodiment, the peptide comprises an amino acid sequence having at least about 90% identity over an entire length of the amino acid sequence of SEQ ID NO: 2, SEQ ID NO: 4, SEQ ID NO: 6, SEQ ID NO: 8, SEQ ID NO: 10 or SEQ ID NO: 12. In one embodiment, the peptide comprises an immunogenic fragment comprising at least about 90% identity over at least 60% of the amino acid sequence of SEQ ID NO: 2, SEQ ID NO: 4, SEQ ID NO: 6, SEQ ID NO: 8, SEQ ID NO: 10 or SEQ ID NO: 12. In one embodiment, the peptide comprises the amino acid sequence of SEQ ID NO: 2, SEQ ID NO: 4, SEQ ID NO: 6, SEQ ID NO: 8, SEQ ID NO: 10 or SEQ ID NO: 12. In one embodiment, the peptide comprises an immunogenic fragment comprising at least 60% of the amino acid sequence of SEQ ID NO: 2, SEQ ID NO: 4, SEQ ID NO: 6, SEQ ID NO: 8, SEQ ID NO: 10 or SEQ ID NO: 12.

In one embodiment, the invention relates to an immunogenic composition comprising a consensus POWV antigen.

In one embodiment, the invention relates to a method of inducing an immune response against a POWV antigen in a subject in need thereof, the method comprising administering an immunogenic composition comprising a nucleic acid molecule encoding at least one consensus POWV antigen to the subject. In one embodiment, the POWV antigen is a prME antigen, a capsid antigen, or a combination thereof. In one embodiment, the administering includes at least one of electroporation and injection.

In one embodiment, the invention relates to a method of treating or preventing a POWV associated pathology in subject in need thereof, the method comprising administering an immunogenic composition comprising a nucleic acid molecule encoding at least one consensus POWV antigen to the subject. In one embodiment, the POWV antigen is a prME antigen, a capsid antigen, or a combination thereof. In one embodiment, the administering includes at least one of electroporation and injection. In one embodiment, the POWV associated pathology is at least one of POWV infection and encephalitis

BRIEF DESCRIPTION OF THE DRAWINGS

FIG. 1, comprising FIG. 1A depicts diagrams of expression constructs developed to express POWV-Cap or Env immunogens. FIG. 1B depicts a diagram demonstrating that consensus POWV immunogens were designed from an analysis of multiple strains of POWV. FIG. 1C depicts exemplary data demonstrating expression of the consensus POWV antigens.

FIG. 2, comprising FIG. 2A depicts diagrams of a single expression construct developed to express POWV Cap and Env immunogens. FIG. 2B depicts exemplary data demonstrating expression of both the cap and env consensus POWV antigens from a single construct.

FIG. 6, comprising FIG. 6A depicts exemplary experimental results demonstrating that the T cell response was reactive to all the Env peptide pools. FIG. 6B depicts exemplary experimental results demonstrating that the T cell response was reactive to all the Cap peptide pools. FIG. 6C depicts the percent intracellular cytokine population for antigen-specific CD4+ and CD8+ T cells. Splenocytes that were stimulated with POWV-envelope peptides spanning the entire length of the protein are evaluated for CD4+ and CD8+ T cells producing IFN-g, IL-2, and TNF-a via flow cytometry. FIG. 6D depicts polyfunctionality of antigen-specific CD4+ and CD8+ T cells. Frequency of total CD4+ and CD8+ T cells expressing double- or triple-positive cytokines (IFN-g, IL-2, and/or TNF-a) using Boolean gating strategy.

FIG. 7, comprising FIG. 7A depicts a diagram of an expression construct for recombinant POWV-envelope protein. FIG. 7B depicts exemplary data demonstrating expression of the POWV-Env recombinant envelope protein. FIG. 7C depicts exemplary experimental data demonstrating the use of a commercial antibody (Pan-Flavivirus) to detect the recombinant POWV-envelope protein.

FIG. 8, comprising FIG. 8A and FIG. 8B depict an ELISA of POWV-SEV immunized murine sera at day 28 (2× immunization). C57BL/6 mice (n=4) were immunized two times at two-week intervals, where 25 μg of POWV-SEV DNA or pMV101 empty vector was delivered intramuscularly (i.m.) using EP-enhanced delivery system. Sera were collected 0, 14 & 28 days post immunization, and half-log dilutions of sera from individual mice were evaluated for their binding capacity to a recombinant POWV-envelope protein at a 1 μg/ml concentration. FIG. 8C depicts the POWV-SEV-specific IgG endpoint titer after each immunization. The antibody endpoint titer was defined as the highest dilution of a serum sample with OD values>(mean+3SD) of vector vaccinated mice. Samples with a titer<50 were given an endpoint titer of 1.

FIG. 9, comprising FIG. 9A depicts a western blot analysis of POWV-SEV immunized murine sera. Pooled day 28 immune sera from the aforementioned experiment was used as a primary antibody to probe POWV-envelope protein and transfected 293T cell lysates as a negative control. FIG. 9B depicts indirect immunofluorescence assay of POWV-SEV transfected Vero cells. Sera obtained from mice immunized with POWV-SEV and the unvaccinated group were diluted 1:50 and tested by the IFA assay. FIG. 9C depicts non-cross-reactivity of POWV-ENV immune sera against ZIKV and WNV antigen. Day 35 POWV-ENV murine immune sera is tested for antigenic cross-reactivity against flaviviruses that are endemic in the U.S.

FIG. 11, comprising

FIG. 14, comprising FIG. 14A depicts antibody mapping of sera from POWV-patients with a recent primary infection POWV with POWV-SEV envelop peptides spanning the entire length of the protein were evaluated specific IgG antibodies detected by ELISA. Day 28 pooled murine immune sera, pMV101 vector control-immunized sera and POWV convalescent patient sera were probed over 74 individual POWV envelop peptides (15-mers with 9 overlapping amino acid sequences). Assessment performed in duplicate. FIG. 14B and FIG. 14C depicts IgG avidity in POWV-SEV avidity compared to POWV convalescent sera. Antibody responses were assessed by ELISA.

DETAILED DESCRIPTION

Figures 1A, 1B, 1C:
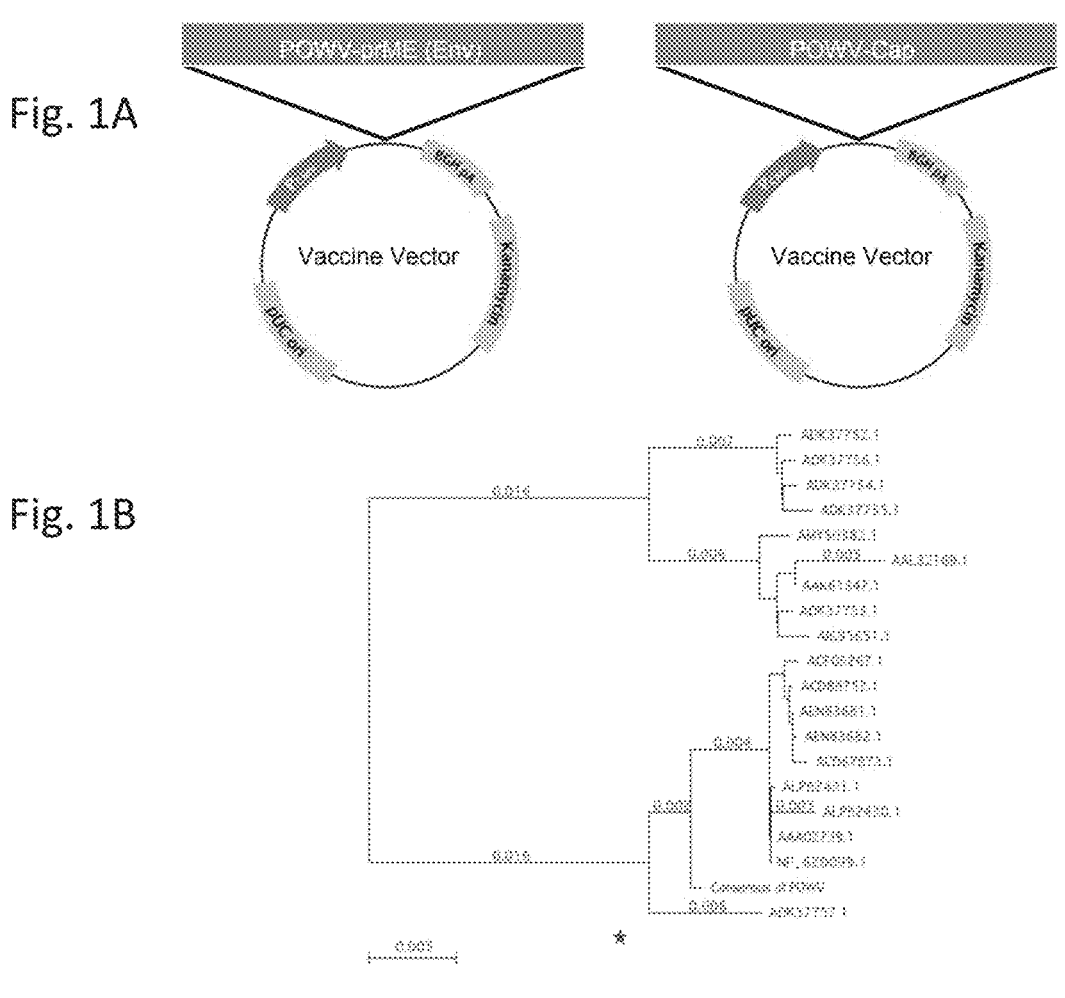
FIG. 1A through FIG. 1C, depicts the design for constructs expressing POWV capsid (Cap) or envelope (Env) immunogens.

The present invention relates to a composition comprising a recombinant nucleic acid sequence that encodes one or more Powassan virus (POWV) antigens, and functional fragments thereof. The composition can be administered to a subject in need thereof to elicit an immune response in the subject against POWV virus.

In one embodiment, the composition comprises one or more nucleotide sequences capable of expressing one or more consensus POWV antigens in the subject and a pharmaceutically acceptable excipient. In one embodiment, the nucleic acid molecule comprises a promoter operably linked to a coding sequence that encodes one or more consensus POWV antigens. In one embodiment, one or more consensus POWV antigens are one or more of pre-membrane and envelope protein (prME) and capsid antigens. In one embodiment, the invention relates to a single nucleic acid construct for expression of both the prME and capsid consensus POWV antigens.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to a nucleic acid vaccine to enhance antigenicity of the vaccine.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antigen as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "consensus sequence" as used herein may mean a synthetic nucleotide sequence, or corresponding polypeptide sequence, constructed based on analysis of an alignment of multiple sequences (e.g., multiple sequences of a particular virus antigen.)

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is effective for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a percentage of a full-length polypeptide sequence or nucleotide sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleotide sequence or amino acid sequence or variant thereof.

"Genetic construct" as used herein refers to the DNA or RNA molecules that comprise a nucleotide sequence which encodes a protein, such as an antigen. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter. SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

The term "subtype" or "serotype" is used herein interchangeably and, in reference to a virus, means genetic variants of that virus antigen such that one subtype is recognized by an immune system apart from a different subtype.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extra chromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Description

The invention is based, in part on the development of an optimized consensus sequence encoding one or more Powassan virus (POWV) antigen. In one embodiment, the one or more POWV antigen encoded by the optimized consensus sequence is capable of eliciting an immune response in a mammal. In one embodiment, the POWV antigen encoded by the optimized consensus sequence can comprise an epitope(s) that makes it particularly effective as an immunogen against which an immune response can be induced.

The optimized consensus sequence can be a consensus sequence derived from two or more POWV antigens. The optimized consensus sequence can comprise a consensus sequence and/or modification(s) for improved expression. Modification can include codon optimization, RNA optimization, addition of a Kozak sequence for increased translation initiation, and/or the addition of an immunoglobulin leader sequence to increase immunogenicity. The POWV antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding non-optimized antigen.

Provided herein are POWV antigens that can be used to induce immunity against POWV in subjects with or at risk of POWV infection. In one embodiment, the present invention provides an immunogenic composition comprising one or more nucleic acid molecules that are capable of generating in a mammal an immune response against a POWV antigen. The present invention also provides isolated nucleic acid molecules that are capable of generating in a mammal an immune response against a POWV antigen. In one embodiment, the nucleic acid molecule comprises an optimized nucleotide sequence encoding a consensus POWV antigen.

Optimized Consensus POWV Antigens

In one embodiment, the present invention provides an immunogenic composition comprising one or more nucleic acid molecules that are capable of generating in a mammal an immune response against a POWV antigen. The present invention also provides isolated nucleic acid molecules that are capable of generating in a mammal an immune response against a POWV antigen. In one embodiment, the nucleic acid molecule comprises an optimized nucleotide sequence encoding at least 1, 2, 3 or more than 3 consensus POWV antigen. In one embodiment, one or more consensus antigens are consensus POWV prME or capsid antigens.

Consensus amino acid sequences for a POWV antigens include SEQ ID NO: 2, SEQ ID NO: 4, SEQ ID NO: 6, SEQ ID NO: 8, SEQ ID NO: 10, SEQ ID NO: 12 and variants thereof and fragments of SEQ ID NO: 2, SEQ ID NO: 4, SEQ ID NO: 6, SEQ ID NO: 8, SEQ ID NO: 10, SEQ ID NO: 12, and variants thereof. An exemplary amino acid sequence of a synthetic consensus POWV prME is provided as SEQ ID NO: 2. An exemplary amino acid sequence of a synthetic consensus POWV prME capsid antigen is provided as SEQ ID NO: 6.

In one embodiment, the invention provides compositions comprising a nucleic acid molecule comprising a nucleotide sequence that encodes a synthetic consensus POWV antigen. In one embodiment, a nucleotide sequence which encodes a synthetic consensus POWV prME antigen is provided as SEQ ID NO: 1, which encodes SEQ ID NO: 2. In one embodiment, a nucleotide sequence which encodes a synthetic consensus POWV capsid antigen is provided as SEQ ID NO: 5, which encodes SEQ ID NO: 6.

In various embodiments, the invention provides compositions comprising a combination of a consensus POWV prME and capsid antigen, or one or more nucleic acid molecules encoding the same. The compositions may comprise a plurality of copies of a single nucleic acid molecule such a single plasmid, or a plurality of copies of two or more different nucleic acid molecules such as two or more different plasmids.

Compositions that comprise one or more nucleotide sequence that encode multiple consensus POWV antigens may be on a single plasmid. In one embodiment, a composition comprises a single plasmid that encodes consensus POWV prME and capsid antigens under a single promoter.

In such an embodiment, the sequence that encodes the prME antigen and the sequence that encodes the capsid antigen may be linked by a fusion peptide sequence, for example a furin cleavage sequence. An exemplary amino acid sequence of a single construct comprising synthetic consensus prME and capsid antigens linked by furin cleavage sites is provided as SEQ ID NO: 10.

In one embodiment, the invention provides compositions comprising a nucleic acid molecule comprising a nucleotide sequence that encodes SEQ ID NO: 10, or a variant or fragment thereof. In one embodiment, the nucleic acid molecule comprises a nucleotide sequence as set forth in SEQ ID NO: 9, or a variant or fragment thereof.

In one embodiment, an optimized consensus encoded POWV antigen is operably linked to one or more regulatory elements. In one embodiment, a regulatory element is a leader sequence. In one embodiment, the leader sequence is an IgE leader sequence. In one embodiment, the IgE leader sequence has an amino acid sequence as set forth in SEQ ID NO: 13. Therefore in one embodiment, the invention relates to an amino acid sequence as set forth in SEQ ID NO: 2, SEQ ID NO: 6 or SEQ ID NO: 10 operably linked to an amino acid sequence as set forth in SEQ ID NO: 13. In one embodiment, the invention relates to a nucleotide sequence encoding an amino acid sequence as set forth in SEQ ID NO: 2, SEQ ID NO: 6 or SEQ ID NO: 10 operably linked to an amino acid sequence as set forth in SEQ ID NO: 13. An exemplary amino acid sequence of a synthetic consensus POWV prME antigen operably linked to an IgE leader sequence is set forth in SEQ ID NO: 4. An exemplary amino acid sequence of a synthetic consensus POWV capsid antigen operably linked to an IgE leader sequence is set forth in SEQ ID NO: 8. An exemplary amino acid sequence of a single construct comprising synthetic consensus POWV prME and capsid antigens linked by furin cleavage sites and further operably linked to an IgE leader sequence is provided as SEQ ID NO: 12. In one embodiment, the invention provides compositions comprising a nucleic acid molecule comprising a nucleotide sequence that encodes SEQ ID NO: 4. SEQ ID NO: 8 or SEQ ID NO: 12, or a variant or fragment thereof. In one embodiment, the nucleic acid molecule comprises a nucleotide sequence as set forth in SEQ ID NO: 3, SEQ ID NO: 7 or SEQ ID NO: 11, or a variant or fragment thereof.

In one embodiment, a regulatory element is a start codon. Therefore, in one embodiment, the invention relates to a nucleotide sequence as set forth in SEQ ID NO: 1, SEQ ID NO: 5, or SEQ ID NO: 9 or a fragment or variant thereof, operably linked to a nucleotide sequence comprising a start codon at the 5' terminus. In one embodiment, the invention relates to an amino acid sequence as set forth in SEQ ID NO: 2, SEQ ID NO: 6, or SEQ ID NO: 10 or a fragment or variant thereof, operably linked to an amino acid encoded by a start codon (e.g., a Methionine) at the N-terminus.

In one embodiment, a regulatory element is at least one stop codon. Therefore, in one embodiment, the invention relates to a nucleotide sequence as set forth in SEQ ID NO: 1. SEQ ID NO: 5, or SEQ ID NO: 9, or a fragment or variant thereof, operably linked to a nucleotide sequence comprising at least one stop codon at the 3' terminus. In one embodiment, the nucleotide sequence is operably linked to two stop codons to increase the efficiency of translational termination.

In one embodiment, nucleic acid molecule can encode a peptide having the amino acid sequence set forth in SEQ ID NO: 2, SEQ ID NO: 4, SEQ ID NO: 6, SEQ ID NO: 8, SEQ ID NO: 10 or SEQ ID NO: 12. In one embodiment, the nucleic acid molecule comprises the nucleotide sequence set forth in SEQ ID NO: 1, SEQ ID NO: 3, SEQ ID NO: 5, SEQ ID NO: 7, SEQ ID NO: 9 or SEQ ID NO: 11. In some embodiments, the sequence can be the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO: 1. SEQ ID NO: 3, SEQ ID NO: 5, SEQ ID NO: 7, SEQ ID NO: 9 or SEQ ID NO: 11. In other embodiments, sequence can be the nucleotide sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 2, SEQ ID NO: 4. SEQ ID NO: 6, SEQ ID NO: 8, SEQ ID NO: 10 or SEQ ID NO: 12.

In some embodiments, the nucleic acid molecule comprises an RNA sequence that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO: 1, SEQ ID NO: 3, SEQ ID NO: 5, SEQ ID NO: 7, SEQ ID NO: 9 or SEQ ID NO: 11. In some embodiments, the nucleic acid molecule comprises an RNA sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence set forth in SEQ ID NO: 2 or SEQ ID NO: 4.

The consensus-POWV antigen can be a peptide having the amino acid sequence set forth in SEQ ID NO: 2, SEQ ID NO: 4, SEQ ID NO: 6, SEQ ID NO: 8, SEQ ID NO: 10 or SEQ ID NO: 12. In some embodiments, the antigen can have an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 2, SEQ ID NO: 4, SEQ ID NO: 6, SEQ ID NO: 8, SEQ ID NO: 10 or SEQ ID NO: 12.

Immunogenic fragments of SEQ ID NO: 2, SEQ ID NO: 4, SEQ ID NO: 6, SEQ ID NO: 8, SEQ ID NO: 10 or SEQ ID NO: 12 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO: 2, SEQ ID NO: 4. SEQ ID NO: 6, SEQ ID NO: 8, SEQ ID NO: 10 or SEQ ID NO: 12. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO: 2, SEQ ID NO: 4, SEQ ID NO: 6, SEQ ID NO: 8, SEQ ID NO: 10 or SEQ ID NO: 12, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO: 2, SEQ ID NO: 4, SEQ ID NO: 6, SEQ ID NO: 8, SEQ ID NO: 10 or SEQ ID NO: 12. Some embodiments relate to immunogenic fragments that have 96% homology to the immunogenic fragments of consensus protein sequences herein.

Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO: 1, SEQ ID NO: 3, SEQ ID NO: 5, SEQ ID NO: 7, SEQ ID NO: 9 or SEQ ID NO: II comprising at least 60%, at least 65%, at least 70%, at least 75%, at least 80%, at least 85%, at least 90%, at least 95%, at least 96%, at least 97%, at least 98% or at least 99% of the full length of SEQ ID NO: 1, SEQ ID NO: 3, SEQ ID NO: 5, SEQ ID NO: 7, SEQ ID NO: 9 or SEQ ID NO: 11. Immunogenic fragments can be at least 96%, at least 97% at least 98% or at least 99% homologous to fragments of SEQ ID NO: 1, SEQ ID NO: 3, SEQ ID NO: 5, SEQ ID NO: 7, SEQ ID NO: 9 or SEQ ID NO: 11. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO: 1. SEQ ID NO: 3, SEQ ID NO: 5, SEQ ID NO: 7, SEQ ID NO: 9 or SEQ ID NO: 11.

In one embodiment, the nucleic acid molecule comprises an RNA sequence encoding a consensus POWV antigen sequence described herein. For example, nucleic acids may comprise an RNA sequence encoding one or more of SEQ ID NO: 2, SEQ ID NO: 4, SEQ ID NO: 6, SEQ ID NO: 8, SEQ ID NO: 10 or SEQ ID NO: 12, a variant thereof, a fragment thereof or any combination thereof.

Nucleic Acid Constructs

When taken up by a cell, the DNA plasmids can remain in the cell as separate genetic material. Alternatively. RNA may be administered to the cell. It is also contemplated to provide a genetic construct as a linear mini chromosome including a centromere, telomeres and an origin of replication. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered. Such genetic constructs may be therefore be recombinant nucleic acid molecules.

The recombinant nucleic acid molecule can include one or more recombinant nucleotide sequence constructs. The recombinant nucleotide sequence construct can include one or more components, which are described in more detail below.

The recombinant nucleotide sequence construct can include a heterologous nucleotide sequence that encodes a viral antigen, a fragment thereof, a variant thereof, or a combination thereof. The recombinant nucleotide sequence construct can also include a heterologous nucleotide sequence that encodes a protease or peptidase cleavage site.

The recombinant nucleotide sequence construct can also include a heterologous nucleotide sequence that encodes an internal ribosome entry site (IRES). An IRES may be either a viral IRES or an eukaryotic IRES. The recombinant nucleotide sequence can include one or more leader sequences, in which each leader sequence encodes a signal peptide. The recombinant nucleotide sequence can include one or more promoters, one or more introns, one or more transcription termination regions, one or more initiation codons, one or more termination or stop codons, and/or one or more polyadenylation signals. The recombinant nucleotide sequence construct can also include one or more linker or tag sequences. The tag sequence can encode a hemagglutinin (HA) tag.

a) Protease Cleavage Site

The recombinant nucleotide sequence construct can include heterologous nucleotide sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a furin cleavage site.

b) Linker Sequence

The recombinant nucleotide sequence construct can include one or more linker sequences. The linker sequence can spatially separate or link the one or more components described herein. In other embodiments, the linker sequence can encode an amino acid sequence that spatially separates or links two or more polypeptides.

c) Promoter

The recombinant nucleotide sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleotide sequence construct as it is from the transcription start site in its natural setting. However, variation in this distance may be accommodated without loss of promoter function.

The promoter may be operably linked to the heterologous nucleotide sequence encoding one or more viral antigen. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metallothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

d) Transcription Termination Region

The recombinant nucleotide sequence construct can include one or more transcription termination regions. The transcription termination region can be downstream of the coding sequence to provide for efficient termination. The transcription termination region can be obtained from the same gene as the promoter described above or can be obtained from one or more different genes.

e) Initiation Codon

The recombinant nucleotide sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

f) Termination Codon

The recombinant nucleotide sequence construct can include one or more termination or stop codons. The termination codon can be downstream of the coding sequence. The termination codon can be in frame with the coding sequence. The termination codon can be associated with one or more signals required for efficient translation termination. Initiation codons and stop codon are generally considered to be part of a nucleotide sequence that encodes the desired protein. However, it is necessary that these elements are functional in the mammals to whom the nucleic acid construct is administered. The initiation and termination codons must be in frame with the coding sequence.

g) Polyadenylation Signal

The recombinant nucleotide sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human $i-globin polyadenylation signal. The SV40 polyadenylation signal may be a polyadenylation signal from a pCEP4 plasmid (Invitrogen, San Diego. CA). Promoters and polyadenylation signals used must be functional within the cells of the individual.

h) Leader Sequence

The recombinant nucleotide sequence construct can include one or more leader sequences. The leader sequence can encode a signal peptide. The signal peptide can be an immunoglobulin (Ig) signal peptide, for example, but not limited to, an IgG signal peptide and a IgE signal peptide.

In addition to regulatory elements required for DNA expression, as described above, other elements may also be included in the recombinant nucleic acid molecule. Such additional elements include enhancers. The enhancer may be selected from the group including but not limited to: human actin, human myosin, human hemoglobin, human muscle creatine and viral enhancers such as those from CMV, RSV and EBV.

Genetic constructs can be provided with mammalian origin of replication in order to maintain the construct extra chromosomally and produce multiple copies of the construct in the cell. Plasmids pMV101, pCEP4 and pREP4 contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons that encode said protein may be selected which are most efficiently transcribed in the host cell. One having ordinary skill in the art can produce DNA constructs that are functional in the cells.

In some embodiments, nucleic acid constructs may be provided in which the coding sequences for the proteins described herein are linked to IgE leader peptide, or such IgE leader is removed. In some embodiments, proteins described herein are linked to IgE signal peptide, or such IgE leader is removed.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well-known expression systems. For example, the commercially available plasmid pSE420 (Invitrogen, San Diego, Calif.) may be used for production of protein in *Escherichia coli* (*E. coli*). The commercially available plasmid pYES2 (Invitrogen, San Diego, Calif.) may, for example, be used for production in *Saccharomyces cerevisiae* strains of yeast. The commercially available MAXBAC™ complete baculovirus expression system (Invitrogen, San Diego, Calif.) may, for example, be used for production in insect cells. The commercially available plasmid pcDNA3.1 or pcDNA3 (Invitrogen, San Diego, Calif.) may, for example, be used for production in mammalian cells such as Chinese hamster ovary (CHO) cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989)). Thus, the desired proteins can be prepared in both prokaryotic and eukaryotic systems, resulting in a spectrum of processed forms of the protein.

Vector

The recombinant nucleotide sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleotide sequence construct is produced by the cellular-transcription and translation machinery ribosomal complexes. The one or more vectors can express large amounts of stable messenger RNA, and therefore proteins.

i) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleotide sequence construct may be chimeric, meaning that at least one of its components is heterologous with respect to at least one of its other components.

j) Plasmid

The one or more vectors can be a plasmid. The plasmid may be useful for transfecting cells with the recombinant nucleotide sequence construct. The plasmid may be useful for introducing the recombinant nucleotide sequence construct into the subject. The plasmid may also comprise a regulatory sequence, which may be well suited for gene expression in a cell into which the plasmid is administered.

k) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to SEQ ID NO: 1, SEQ ID NO: 3, SEQ ID NO: 5, SEQ ID NO: 7, SEQ ID NO: 9 or SEQ ID NO: 11. In another embodiment, the nucleotide sequence comprises an RNA sequence transcribed by a DNA sequence encoding a polypeptide sequence of SEQ ID NO: 2, SEQ ID NO: 4, SEQ ID NO: 6, SEQ ID NO: 8, SEQ ID NO: 10 or SEQ ID NO: 12, or a variant thereof or a fragment thereof. Accordingly, in one embodiment, the invention provides an RNA molecule encoding one or more consensus POWV antigen. The RNA may be plus-stranded. Accordingly, in some embodiments, the RNA molecule can be translated by cells without needing any intervening replication steps such as reverse transcription. An RNA molecule useful with the invention may have a 5' cap (e.g. a 7-methylguanosine). This cap can enhance in vivo translation of the RNA. The 5' nucleotide of an RNA molecule useful with the invention may have a 5' triphosphate group. In a capped RNA this may be linked to a 7-methylguanosine via a 5'-to-5' bridge. An RNA molecule may have a 3' poly-A tail. It may also include a poly-A polymerase recognition sequence (e.g. AAUAAA) near its 3' end. An RNA molecule useful with the invention may be single-stranded. An RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

l) Circular and Linear Vector

The one or more vectors may be circular plasmid, which may transform a target cell by integration into the cellular genome or exist extra chromosomally (e.g., autonomous replicating plasmid with an origin of replication). The vector can be pVAX1, pMV101, pcDNA3.0, or provax, or any other expression vector capable of expressing the heavy chain polypeptide and/or light chain polypeptide encoded by the recombinant nucleotide sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleotide sequence construct. The LEC may be any linear DNA devoid of any phosphate backbone. The LEC may not contain any antibiotic resistance genes and/or a phosphate backbone. The LEC may not contain other nucleotide sequences unrelated to the desired gene expression.

The LEC may be derived from any plasmid capable of being linearized. The plasmid may be capable of expressing the heavy chain polypeptide and/or light chain polypeptide encoded by the recombinant nucleotide sequence construct. The plasmid can be pNP (Puerto Rico/34) or pM2 (New Caledonia/99). The plasmid may be WLV009, pVAX1, pMV101, pcDNA3.0, or provax, or any other expression vector capable of expressing the heavy chain polypeptide and/or light chain polypeptide encoded by the recombinant nucleotide sequence construct.

The LEC can be pcrM2. The LEC can be pcrNP, pcrNP and pcrMR can be derived from pNP (Puerto Rico/34) and pM2 (New Caledonia/99), respectively.

m) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian. e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585, 362.

n) Method of Preparing the Vector

Provided herein is a method for preparing the one or more vectors in which the recombinant nucleotide sequence construct has been placed. After the final subcloning step, the vector can be used to inoculate a cell culture in a large-scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

2. Vaccines and Immunogenic Compositions

Immunogenic compositions, such as vaccines, are provided comprising an optimized consensus sequence, an optimized consensus-encoded antigen, a fragment thereof, a variant thereof, or a combination thereof. The immunogenic composition can significantly induce an immune response of a subject administered with the immunogenic composition against the POWV antigen. The vaccine may comprise a plurality of the nucleic acid molecules, or combinations thereof. The vaccine may be provided to induce a therapeutic or prophylactic immune response.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more POWV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790.987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the viruses. The immunogenic compositions are comprised of one or more nucleic acid molecules capable of expressing a consensus viral antigens in the mammal.

In one embodiment, the immunogenic composition comprises a nucleotide sequence that encodes at least one consensus POWV antigen. The consensus viral antigens may be consensus envelope, consensus capsid, prME, NS1, NS2A, NS2B, NS3, NS4A, NS4B, NS5, or a fusion of one or more of aforementioned antigens.

Each antigen can be associated with viral infection. In one embodiment, each antigen can be associated with a POWV virus infection.

The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

In some embodiments, the immunogenic composition comprises a plurality of unique nucleic acid molecules, wherein each of the plurality of unique nucleic acid molecules encodes a consensus E protein, consensus prME, or consensus capsid protein.

Exemplary nucleic acid molecules that can be included in the immunogenic composition of the invention may be selected from:

| SEQ ID NO: | Type | Description |
|---|---|---|
| 1 | Nucleotide | Consensus POWV prME antigen |
| 2 | Amino Acid | Consensus POWV prME antigen |
| 3 | Nucleotide | Consensus POWV prME antigen operably linked to an IgE leader sequence |
| 4 | Amino Acid | Consensus POWV prME antigen operably linked to an IgE leader sequence |
| 5 | Nucleotide | Consensus POWV capsid antigen |
| 6 | Amino Acid | Consensus POWV capsid antigen |
| 7 | Nucleotide | Consensus POWV capsid antigen operably linked to an IgE leader sequence |
| 8 | Amino Acid | Consensus POWV capsid antigen operably linked to an IgE leader sequence |
| 9 | Nucleotide | Consensus POWV capsid + prME antigen |
| 10 | Amino Acid | Consensus POWV capsid + prME antigen |
| 11 | Nucleotide | Consensus POWV capsid + prME antigen operably linked to an IgE leader sequence |
| 12 | Amino Acid | Consensus POWV capsid + prME antigen operably linked to an IgE leader sequence | vaccine itself does not cause illness or death; being protective against illness; inducing protective T cell responses; and providing ease of administration, few side effects, biological stability, and low cost per dose.

Provided herein is an immunogenic composition capable of generating in a mammal an immune response against POWV. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more consensus POWV antigen. Immunogenic compositions are preferably compositions comprising plasmids.

Another aspect of the present invention provides immunogenic compositions that are capable of generating in a mammal an immune response against one or more POWV In one embodiment, the nucleic acid molecule comprises a optimized nucleic acid sequence. The optimized sequence can comprise a consensus sequence and/or modification(s) for improved expression. Modification can include codon optimization. RNA optimization, addition of a Kozak sequence for increased translation initiation, and/or the addition of an immunoglobulin leader sequence to increase immunogenicity. The POWV antigen encoded by the optimized sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The POWV antigen encoded by the optimized sequence can be designed to elicit stronger cellular and/or humoral immune responses than a corresponding native antigen.

The immunogenic composition can induce an immune response in the subject administered the composition. The induced immune response can be specific for at least one POWV antigen. The induced immune response can be reactive with at least one POWV antigen related to an administered optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for at least one POWV antigen. The induced humoral immune response can be reactive with at least one POWV antigen related to an administered optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition of the invention.

The humoral immune response induced by the immunogenic composition can include an increased level of IgG antibodies associated with the subject administered the immunogenic composition as compared to a subject not administered the immunogenic composition. These IgG antibodies can be specific for at least one POWV antigen genetically related to an administered optimized consensus-encoded antigen. These IgG antibodies can be reactive with at least one POWV antigen genetically related to an administered optimized consensus-encoded antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition.

The immunogenic composition can induce a cellular immune response in the subject administered the immunogenic composition. The induced cellular immune response can be specific for at least one POWV antigen genetically related to an administered optimized consensus-encoded antigen. The induced cellular immune response can be reactive at least one POWV antigen genetically related to an administered optimized consensus-encoded antigen. The induced cellular immune response can include eliciting a CD8+ T cell response. The elicited CD8+ T cell response can be reactive with at least one POWV antigen genetically related to an administered optimized consensus-encoded antigen. The elicited CD8+ T cell response can be polyfunctional. The induced cellular immune response can include eliciting a CD8+ T cell response, in which the CD8+ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8+ T cell response associated with the subject administered the immunogenic composition as compared to the subject not administered the immunogenic composition. The CD8+ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition.

The induced cellular immune response can include an increased frequency of CD107a/IFN$\gamma$/T-bet triple-positive CD8 T cells that are reactive against the native antigen. The frequency of CD107a/IFN$\gamma$/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition.

The induced cellular immune response can include an increased frequency of CD107a/IFN$\gamma$ double-positive CD8 T cells that are reactive against the native antigen. The frequency of CD107a/IFN$\gamma$ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition.

The cellular immune response induced by the immunogenic composition can include eliciting a CD4+ T cell response. The elicited CD4+ T cell response can be reactive with the native antigen genetically related to the optimized consensus antigen. The elicited CD4+ T cell response can be polyfunctional. The induced cellular immune response can include eliciting a CD4+ T cell response, in which the CD4+ T cells produce IFN-γ. TNF-α, IL-2, or a combination of IFN-γ and TNF-α.

The induced cellular immune response can include an increased frequency of CD4+ T cells that produce IFN-γ. The frequency of CD4+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition.

The induced cellular immune response can include an increased frequency of CD4+ T cells that produce TNF-α. The frequency of CD4+TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold. 14-fold, 15-fold, 16-fold, 17-fold, 18-fold, 19-fold, 20-fold, 21-fold, or 22-fold as compared to a subject not administered the immunogenic composition.

The induced cellular immune response can include an increased frequency of CD4+ T cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition.

Other Components of the Composition

In some embodiments, the immunogenic composition of the invention further includes a pharmaceutically acceptable excipient. A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in US. Ser. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some embodiments of the present invention, the immunogenic compositions can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

The immunogenic compositions according to the present invention are formulated according to the mode of administration to be used. In cases where DNA plasmid vaccines are injectable compositions, they are sterile, and/or pyrogen free and/or particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

In some embodiments, the transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS). Freunds incomplete adjuvant. LPS analog including monophosphoryl lipid A, muramyl peptides, quinone analogs and vesicles such as squalene and squalene, and hyaluronic acid may also be used administered in conjunction with the composition. The composition may also include transfection facilitating agents such as lipids, liposomes, including lecithin liposomes or other liposomes known in the art, as a DNA-liposome mixture (see for example WO09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise nucleic acid at quantities of from about 1 nanogram to 100 milligrams; about 1 microgram to about 10 milligrams; or preferably about 0.1 microgram to about 10 milligrams; or more preferably about 1 milligram to about 2 milligrams. In some preferred embodiments, composition according to the present invention comprises about 5 nanograms to about 1000 micrograms of nucleic acid. In some preferred embodiments, composition can contain about 10 nanograms to about 800 micrograms of nucleic acid. In some preferred embodiments, the composition can contain about 0.1 to about 500 micrograms of nucleic acid. In some preferred embodiments, the composition can contain about 1 to about 350 micrograms of nucleic acid. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanograms to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of nucleic acid.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

Methods of Delivery of the Composition

Another aspect of the present invention provides methods of eliciting an immune response against one or more POWV virus in a mammal, comprising delivering an immunogenic composition to tissue of the mammal, the an immunogenic composition comprising at least one nucleic acid molecule capable of expressing a consensus antigen of the one or more POWV virus in a cell of the mammal to elicit an immune response in the mammal.

The present invention also relates to methods of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices. "microprojectile bombardment gone guns", or other physical methods such as electroporation ("EP"), "hydro-dynamic method", or ultrasound.

Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000. U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Method of Treatment

Also provided herein is a method of treating, protecting against, and/or preventing disease in a subject in need thereof by inducing an immune response against a viral antigen in the subject. In certain embodiments, the invention provides a method of treating, protecting against, and/or preventing at least one of a POWV virus infection or a POWV associated pathology in a subject. In one embodiment, a POWV associated pathology is encephalitis.

The method can include administering an immunogenic composition of the invention to the subject. Administration of the composition to the subject can be done using the method of delivery described above.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

Combination Vaccine

The present invention also provides a method of treating, protecting against, and/or preventing disease in a subject in need thereof by administering a combination of two or more nucleic acid molecules or immunogenic compositions wherein each of the two or more nucleic acid molecules or immunogenic compositions encodes an optimized consensus viral antigen.

The two or more nucleic acid molecules or immunogenic compositions may be administered using any suitable method such that a combination of two or more nucleic acid molecules or immunogenic compositions are both present in the subject. In one embodiment, the method may comprise administration of a first nucleic acid molecule or immunogenic composition of the invention by any of the methods described in detail above and administration of a second nucleic acid molecule or immunogenic composition less than 1, less than 2, less than 3, less than 4, less than 5, less than 6, less than 7, less than 8, less than 9 or less than 10 days following administration of the first nucleic acid molecule or immunogenic composition of the invention. In one embodiment, the method may comprise administration of at least 2, at least 3, at least 4, at least 5, at least 6 or more than 6 nucleic acid molecules or immunogenic compositions concurrently at different sites on the same subject. In one embodiment, the method may comprise administration of at least 2, at least 3, at least 4, at least 5, at least 6 or more than 6 nucleic acid molecules or immunogenic compositions more than 1, more than 2, more than 3, more than 4, more than 5, more than 6, more than 7, more than 8, more than 9 or more than 10 days following administration of a first nucleic acid molecule or immunogenic composition. In one embodiment, the method may comprise administration of at least 2, at least 3, at least 4, at least 5, at least 6 or more than 6 nucleic acid molecules or immunogenic compositions less than 1, less than 2, less than 3, less than 4, less than 5, less than 6, less than 7, less than 8, less than 9 or less than 10 days following administration of a first nucleic acid molecule or immunogenic composition.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with a muscle or skin EP device described herein have high DNA concentrations, preferably concentrations that include microgram to tens of milligram quantities, and preferably milligram quantities, of DNA in small volumes that are optimal for delivery to the skin, preferably small injection volume, ideally 25-200 microliters (µL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 µL of formula, and more preferably gram quantities of DNA in 100 µL of formula.

The DNA plasmids for use with the EP devices of the present invention can be formulated or manufactured using a combination of known devices and techniques, but preferably they are manufactured using an optimized plasmid manufacturing technique that is described in U.S. application Ser. No. 12/126,611 which published as US Publication No. 20090004716, which published Jan. 1, 2009. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in US Publication No. 20090004716 and those described in U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The publications, US Publication No. 20090004716 and U.S. Pat. No. 7,238,522, are hereby incorporated in their entirety.

Example 1: Construction & Characterization of Immune Responses to Novel Synthetic DNA Vaccines Against Powassan Virus DNA vaccines have been developed to elicit the immune responses against consensus viral proteins of various emerging infectious diseases. The current invention demonstrates the development and use of a Powassan vaccine to induce an immune response in a vaccinated subject.

The materials and methods used are now described

Plasmid Vaccine Constructions

Plasmids were developed to express consensus POWV prME or POWV capsid antigens (FIG. 1) or a combination of consensus POWV capsid and prME antigens (FIG. 2).

Animals and Vaccinations

Figures 2A, 2B, 3:
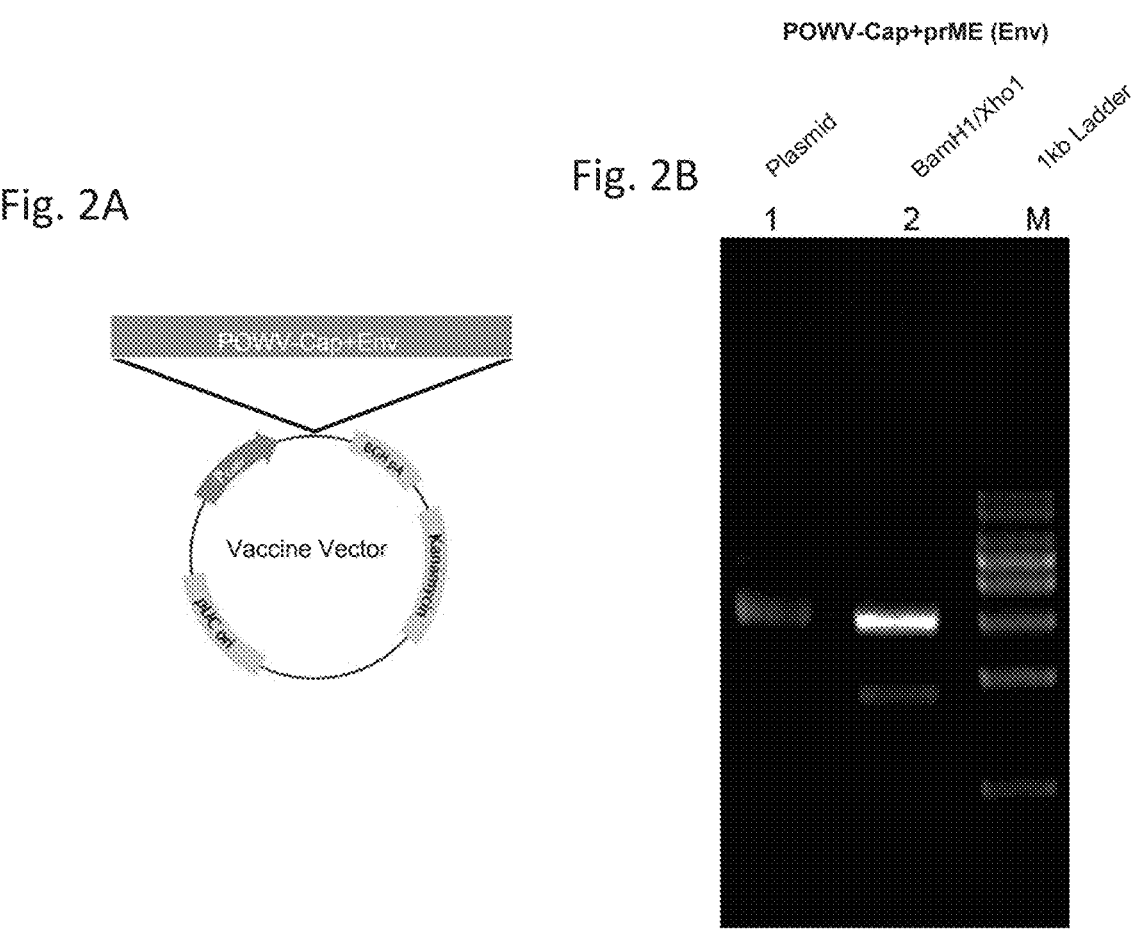
FIG. 2A through FIG. 2B, depicts the design for constructs expressing POWV capsid (Cap) and envelope (Env) immunogens.
FIG. 3 depicts an exemplary immunization schedule for POWV vaccines. Balb/C mice were immunized with POWV-Env, POWV-Cap, POWV-Cap+Env or pMV101, with electroporation (EP) 2 times every 2 weeks. Sera and Splenocytes from individual mice (n=4) were isolated 1 week after the second immunization. ELISA and ELISpot assays were performed to measure the humoral and cellular immune responses.

Balb/C mice were immunized with POWV-Env, POWV-Cap. POWV-Cap+Env or pMV101, with electroporation (EP) 2 times every 2 weeks. Sera and Splenocytes from individual mice (n=4) were isolated 1 week after the second immunization (FIG. 3).

The results of the experiments are now described

POWV DNA Vaccine Immunogenicity in Mice

Figure 4:
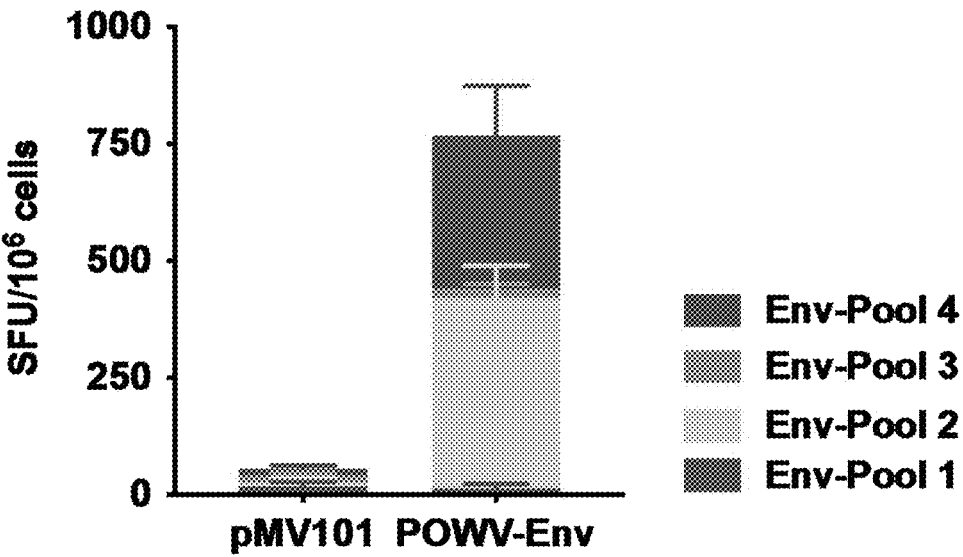
FIG. 4 depicts the results of an exemplary POWV-Env IFN-γ ELISpot assay showing a robust T cell response in POWV-Env vaccinated animals. The T cell response was reactive to all the peptide pools.
Figure 5:
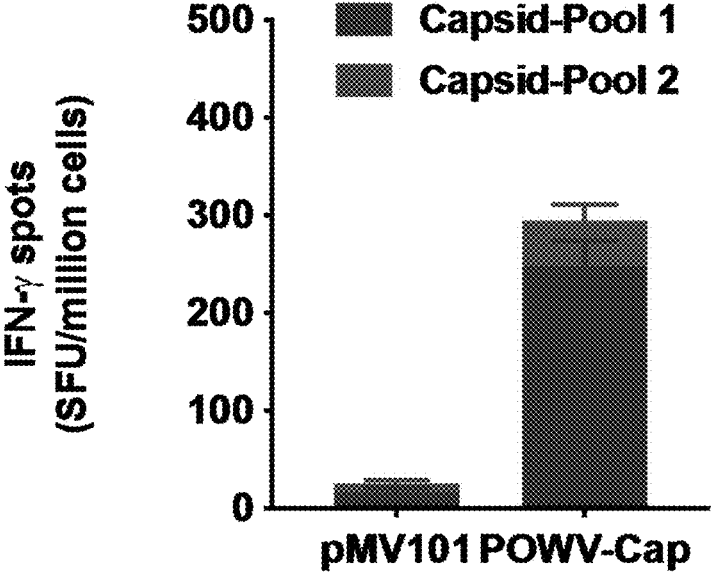
FIG. 5 depicts the results of an exemplary POWV-Cap IFN-γ ELISpot assay showing a robust T cell response in POWV-Capsid vaccinated animals.
Figure 6A:
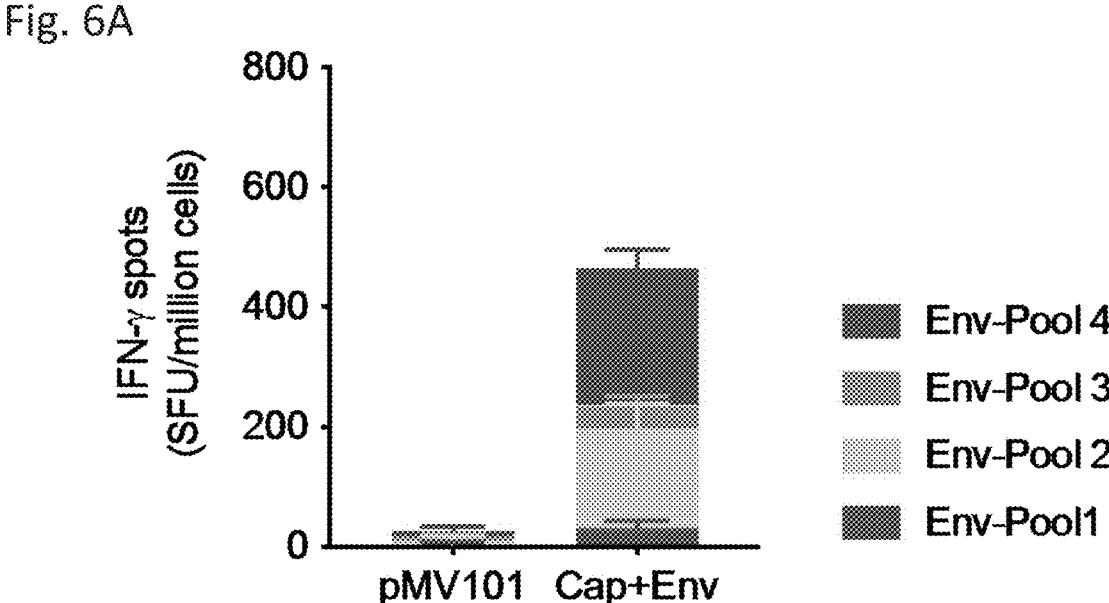
FIG. 6A through FIG. 6D, depicts the results of an exemplary POWV-Cap+Env IFN-γ ELISpot assay showing a robust T cell response in POWV-Cap+Env vaccinated animals.
Figure 6B:
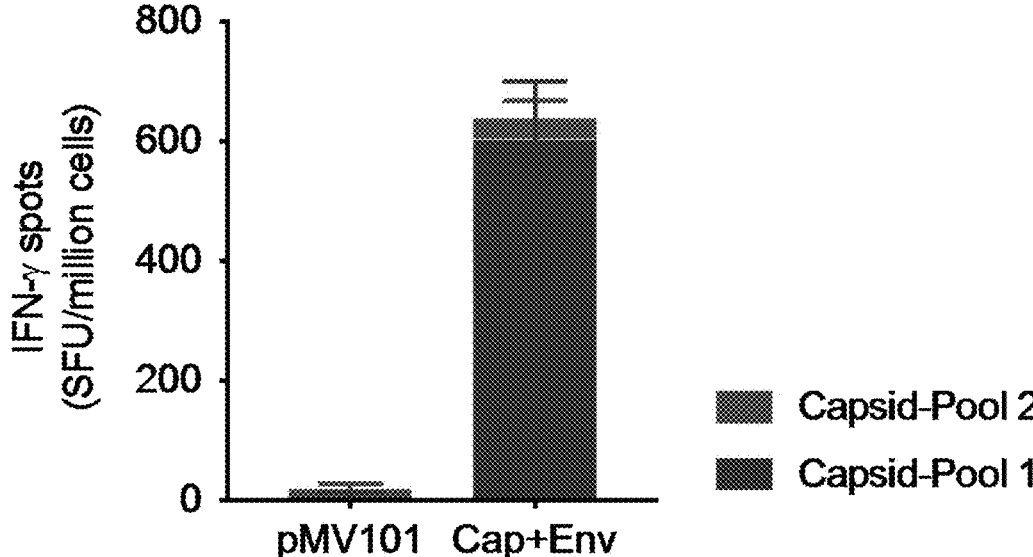
Figure 6C:
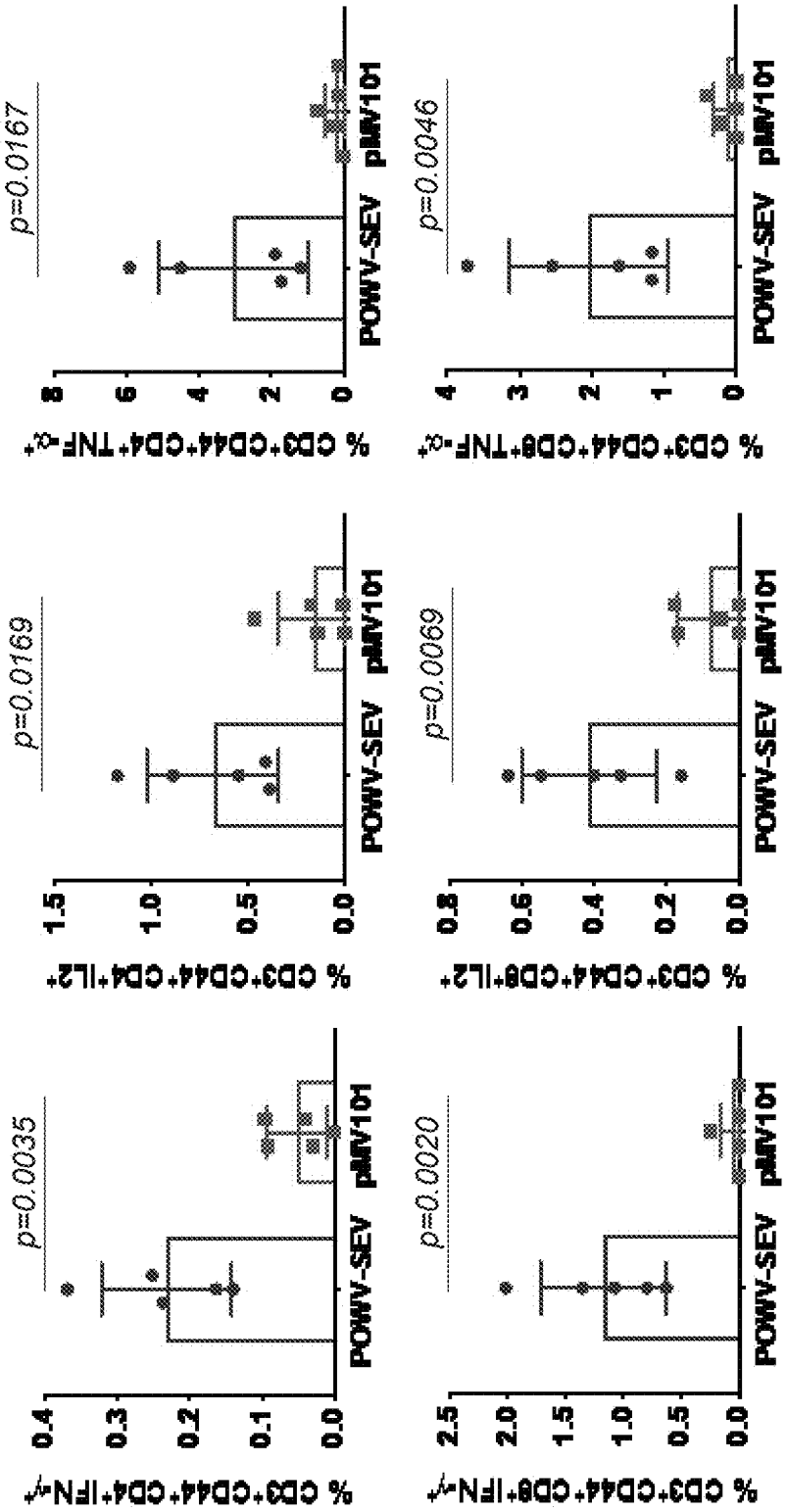
Figure 6D:
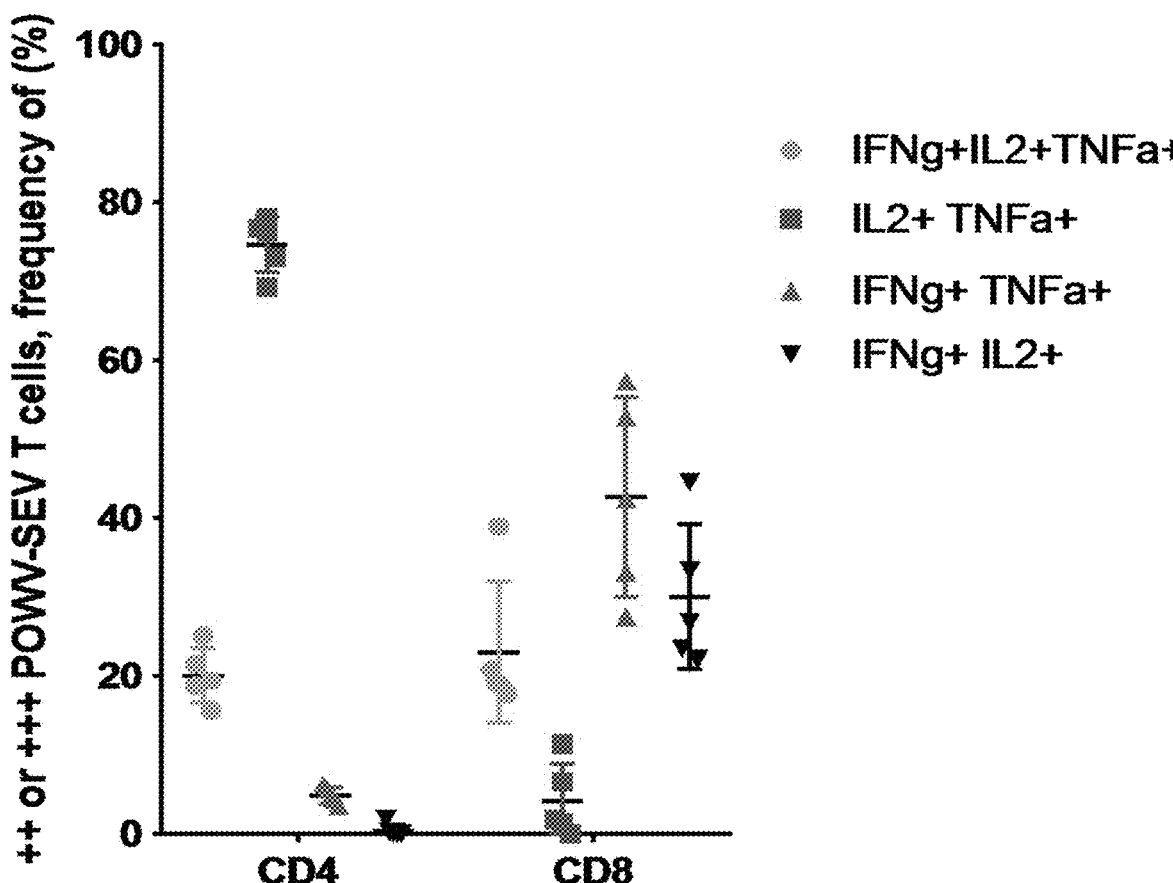
Figure 7A:
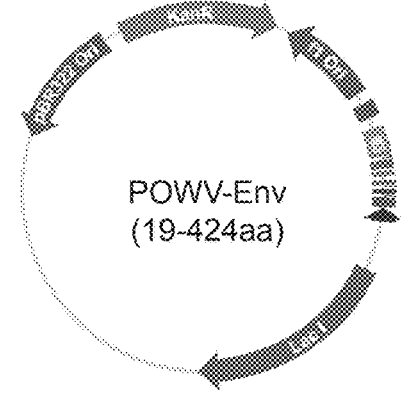
FIG. 7A through FIG. 7C, depicts exemplary experimental results demonstrating the generation of a POWV-Env recombinant envelope protein.
Figure 7B:
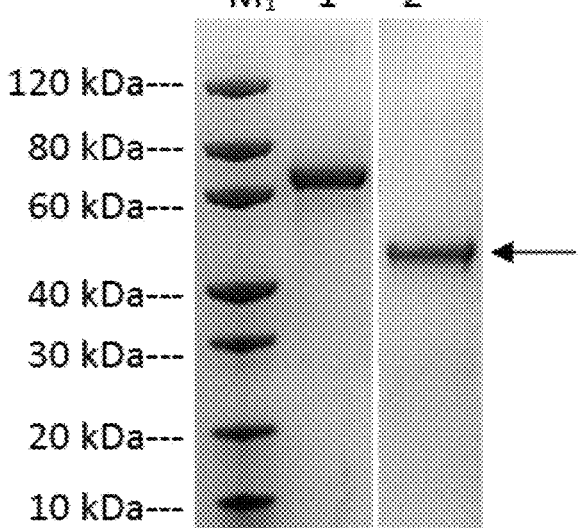
Figure 7C:
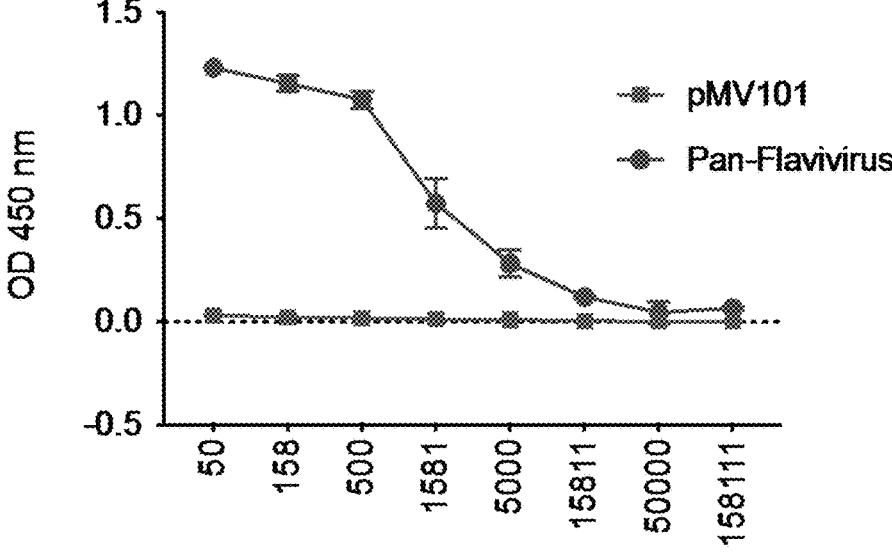
Figure 8A:
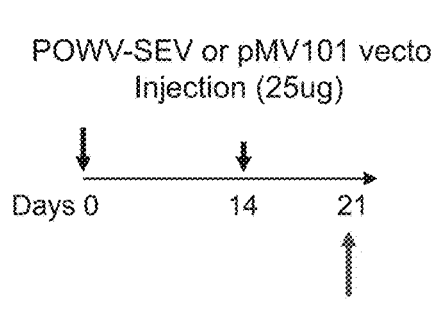
FIG. 8A through FIG. 8C, depicts exemplary data demonstrating the POWV-SEV vaccine induces antigen-specific, functionally binding antibodies in mice.
Figure 8B:
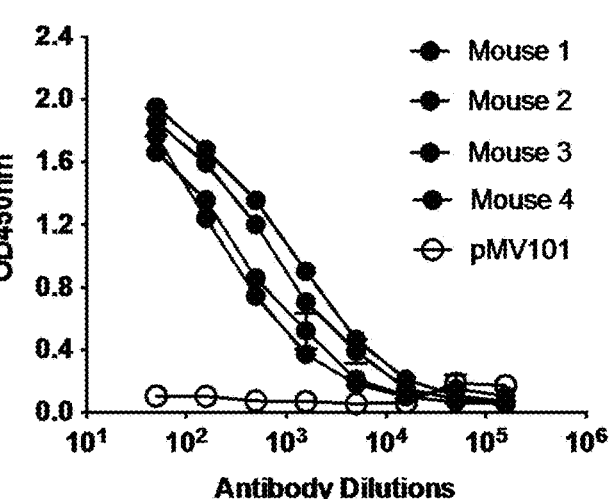
Figure 8C:
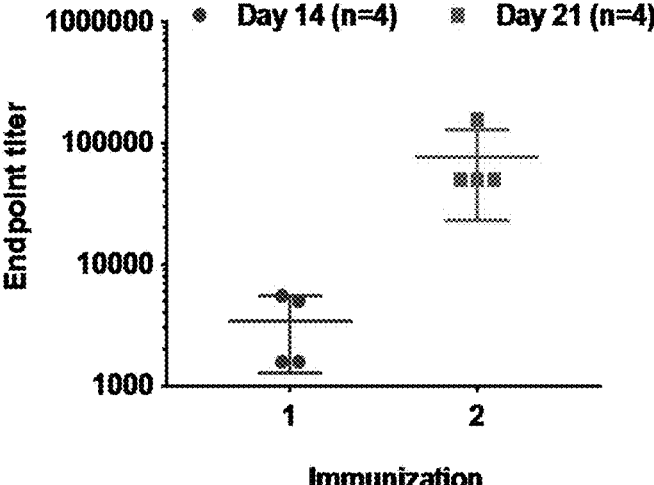
Figure 9A:
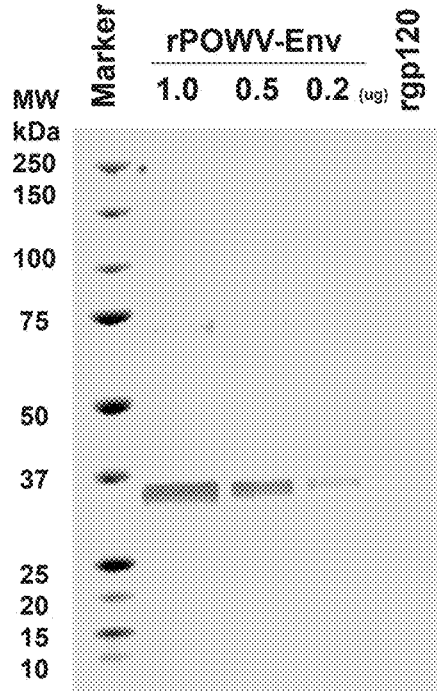
FIG. 9A through FIG. 9C, depicts exemplary data demonstrating that POWV-SEV vaccine induces antigen-specific, functionally binding antibodies in mice.
Figure 9C:
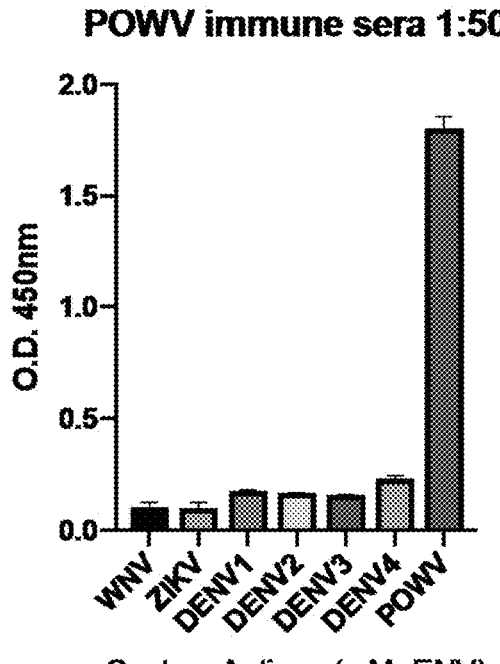
Figure 9B:
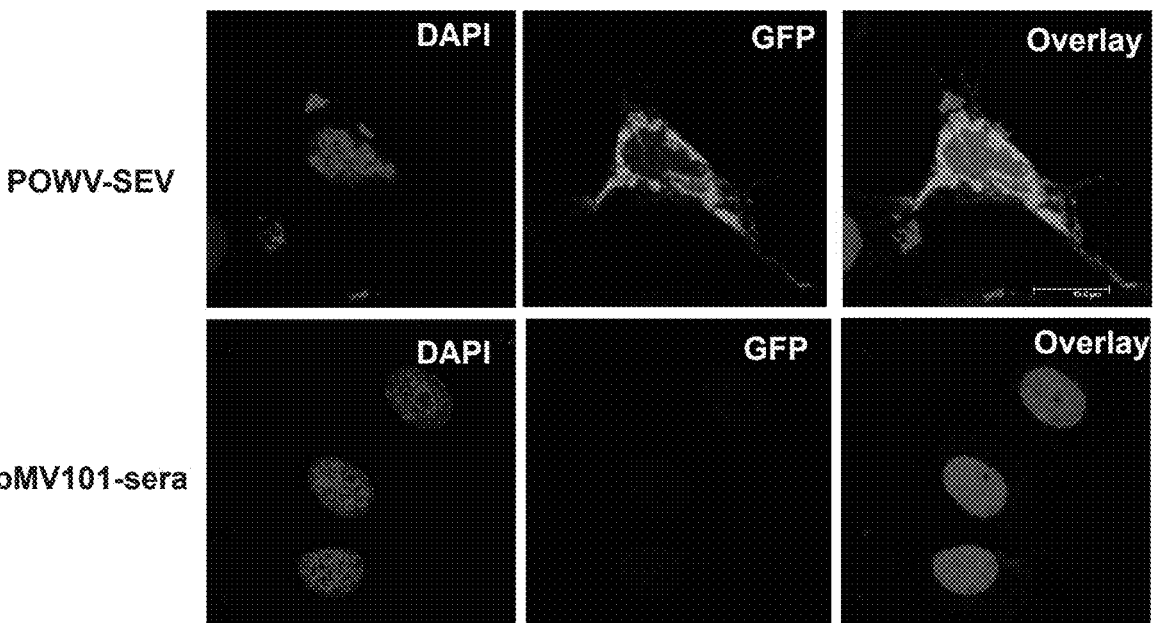
Figure 10:
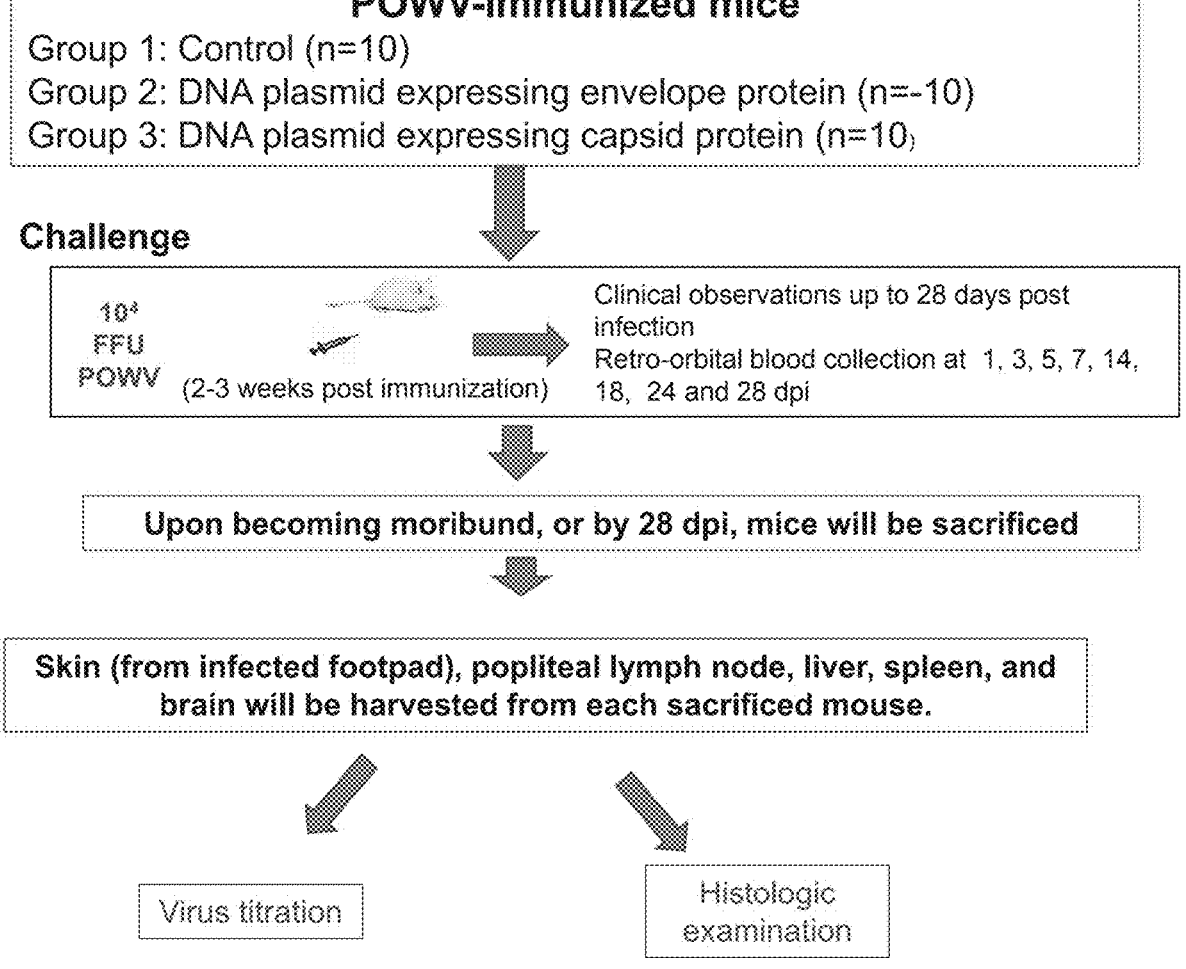
FIG. 10 is an image showing the proposed POWV-challenge studies for the POWV-DNA vaccine.
Figure 11A:
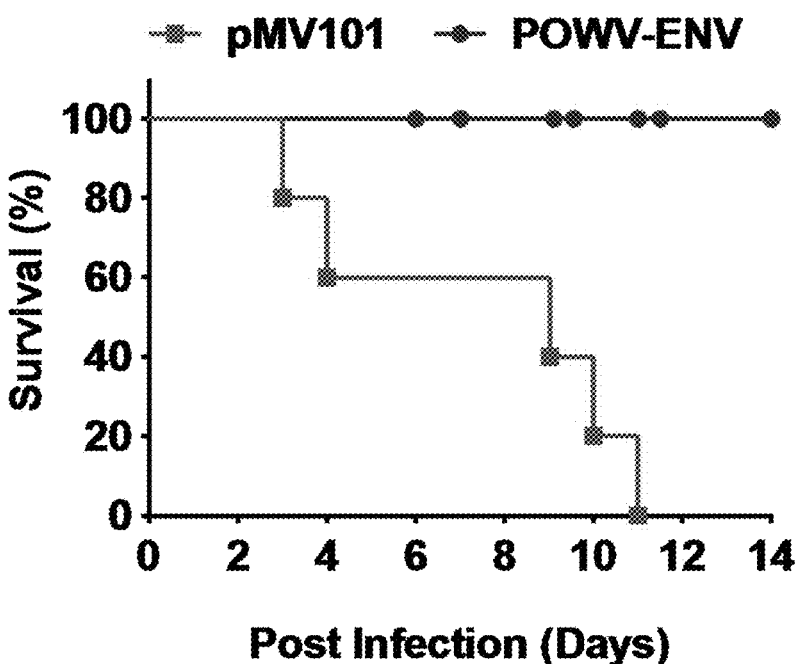
FIG. 11A and FIG. 11B, depicts exemplary data demonstrating that the vaccine protects against lethal challenge with POWV. It was observed that POWV-Env based vaccine delivered 1× were all effective in conferring protective immunity against the POWV-viral challenge.
Figure 11B:
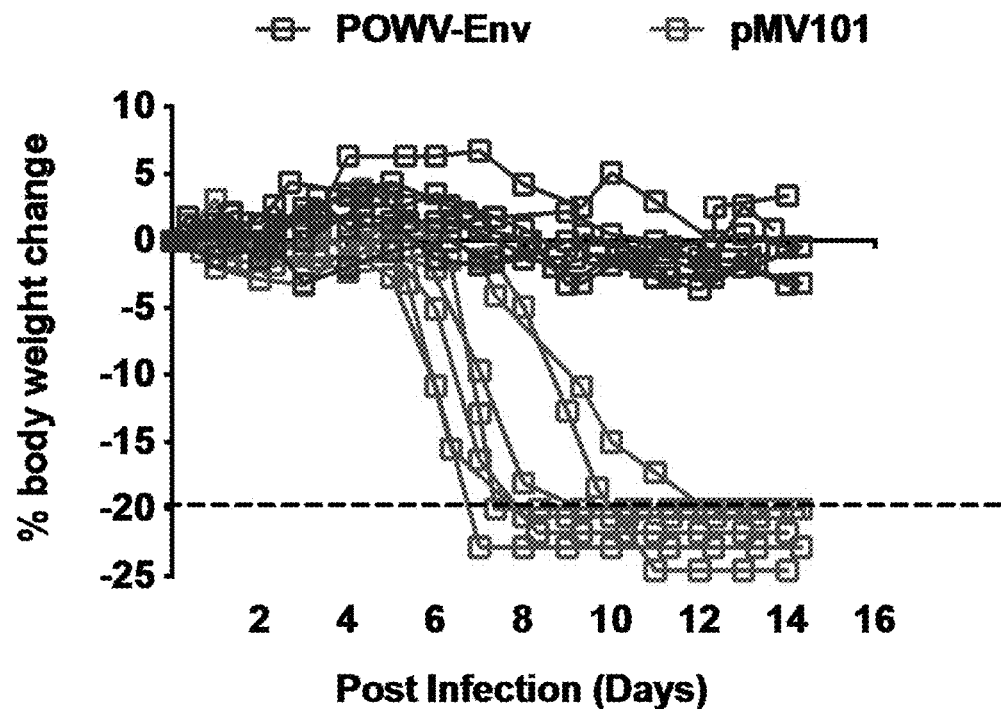
Figure 12:
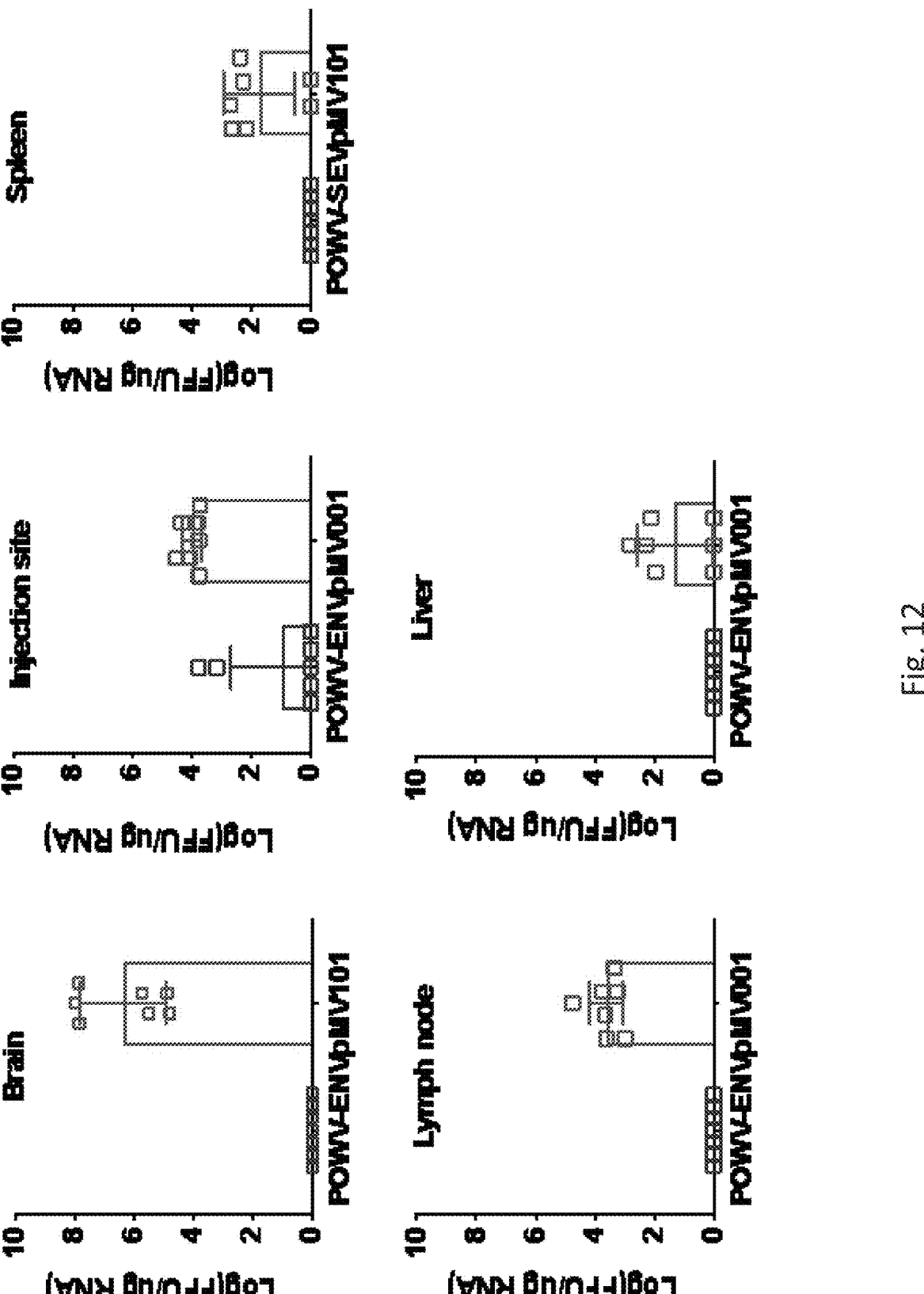
FIG. 12 depicts exemplary data demonstrating the POWV viral burden in organs of pMV101- or POWV-SEV vaccinated mice at endpoint.
Figure 13:
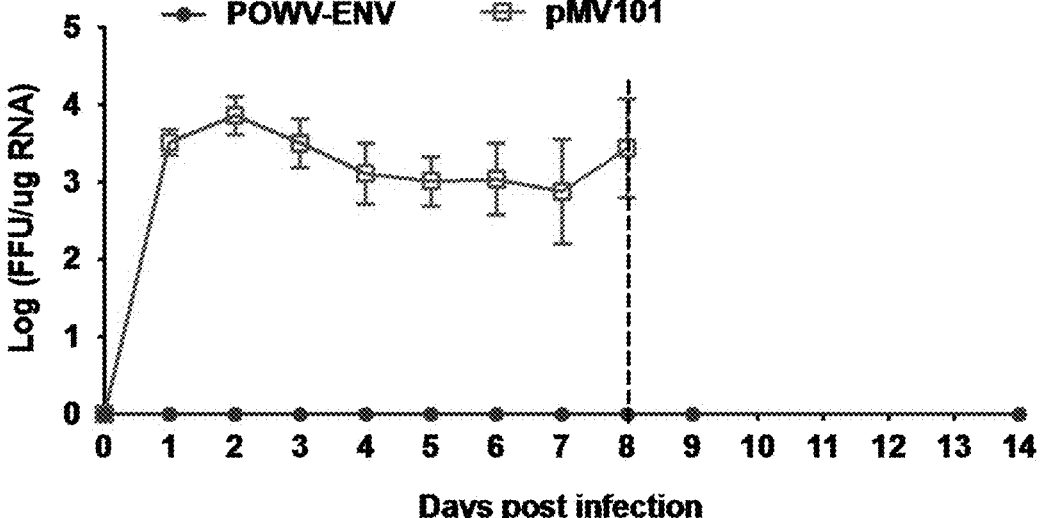
FIG. 13 depicts exemplary data demonstrating the kinetics of circulating peripheral blood viral load of pMV101- or POWV-SEV-vaccinated C57Bl/6 mice upon challenge (n 7) depicting average FFU/ug RNA of each cohort. The dotted line indicates the average survival in days for control pMV101 vaccinated mice upon challenge.
Figure 14A:
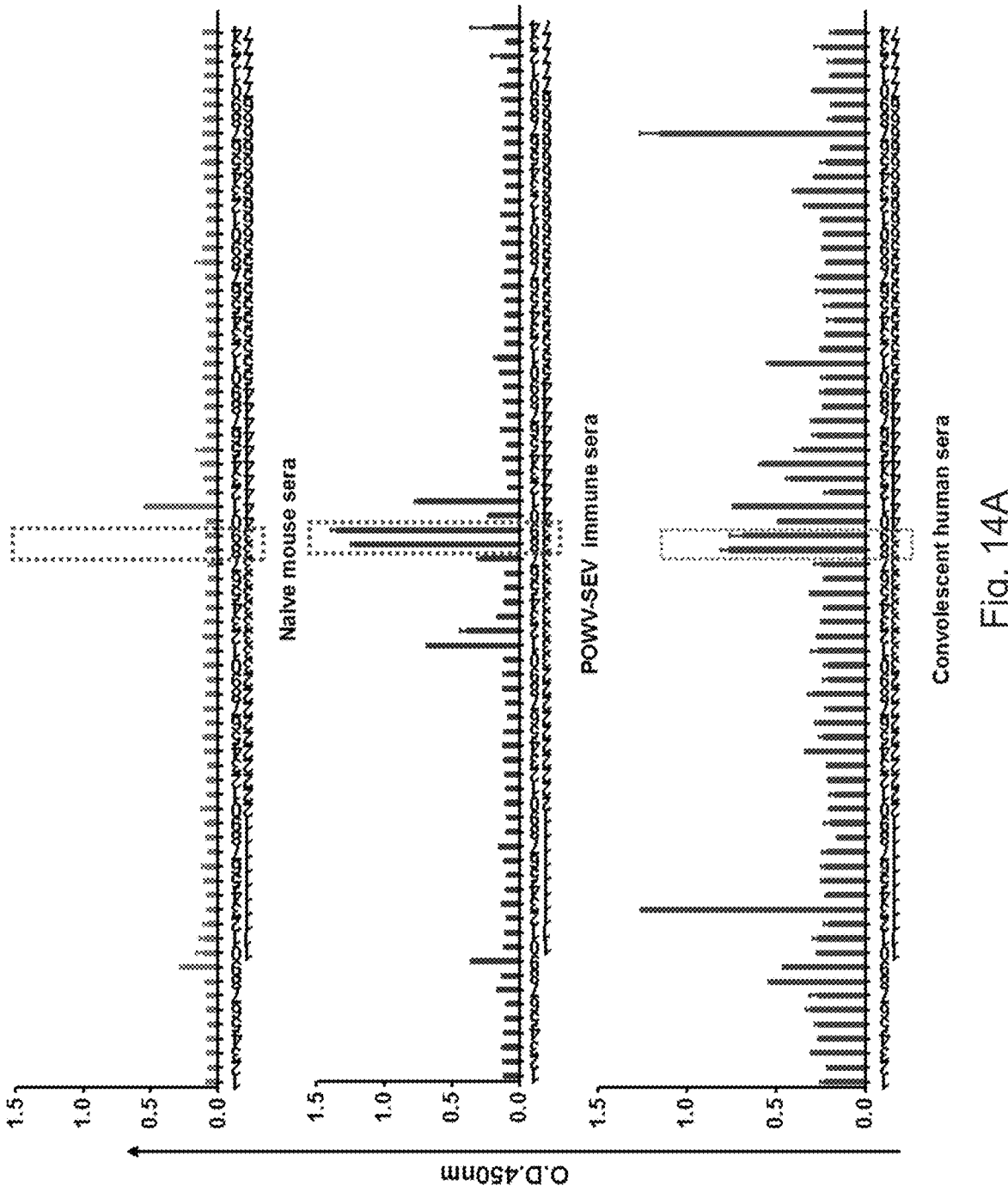
FIG. 14A through FIG. 14C, depicts exemplary data demonstrating that POWV-SEV-induced immune sera are comparable to POWV convalescent patient serum. IgG antibodies and IgG avidity were detected in POWV-convalescent patient sera and POWV-SEV immunized sera.
Figures 14B, 14C:
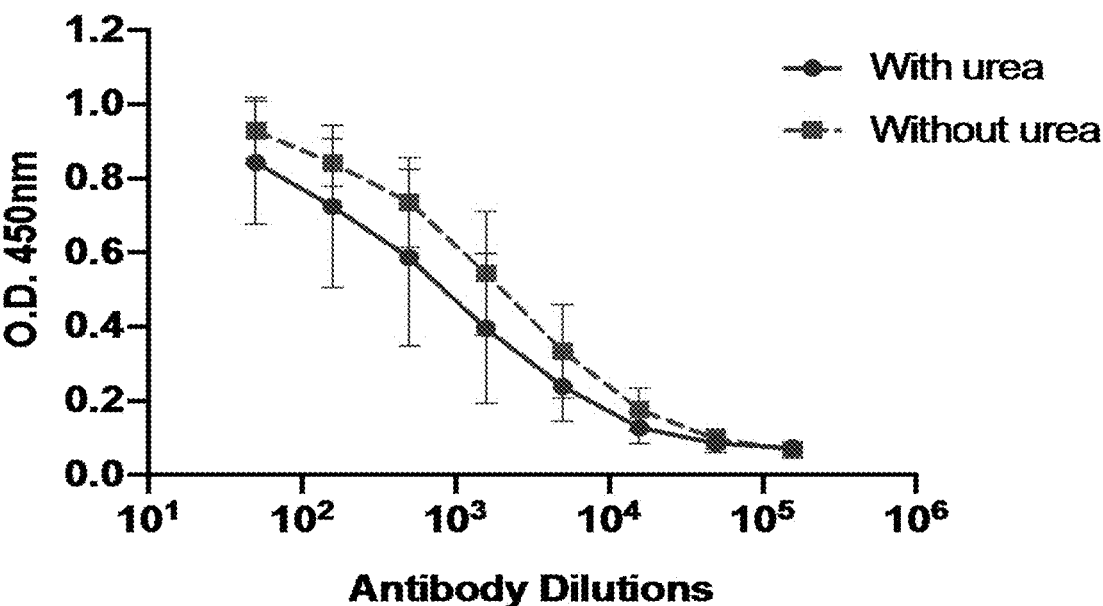

Immunogenicity and protective efficacy of POWV DNA vaccines were evaluated in mice. Mice which received three immunizations by IM-EP delivery of 25 µg pPOWV. Cellular responses were measured by splenocyte IFNγ ELISpot one week after final immunization. As shown in FIG. 4 through FIG. 6. POWV vaccine induced strong IFN-γ response against POWV. Antigen binding IgG ELISAs were performed to evaluate humoral immune responses in mice. The POWV vaccine induced strong binding antibodies (FIG. 8 and FIG. 9). Further, the data presented in FIG. 10-FIG. 13 demonstrates that immunization with POWV-prME DNA vaccine confers protective efficacy. Finally, the data provided in FIG. 14 demonstrates that POWV-SEV-induced immune sera are comparable to POWV convalescent patient serum. These data indicated that the POWV DNA vaccine is immunogenic in mice provides support for further testing in larger animal species.

Example 2: Eliciting Protective Immune Responses by Synthetic Engineered DNA Vaccine Against Powassan Virus Powassan virus (POWV) is an emerging RNA virus that belongs to the tick-borne flavivirus (TBFV), spread to humans by the bite of an infected tick. The incidence of POWV infection in the past 16 years has increased nearly 300% compared to the last four decades since its discovery in 1958. POWV can be transmitted to humans in as little as 15 minutes compared to contracting Lyme disease that requires the tick to be attached for 24-48 hours. POWV infection can produce severe neurological sequalae, meningitis, and encephalitis, leading to death due to lymphocytes infiltrating the central nervous system. Although the prevalence is still low, climate change is rapidly expanding the range of the viremic vectors, threatening and predicting a rise in prevalence. Based on the increasing occurrence of POWV infection, NIAID has recently designated this virus a category C pathogen. Despite the potential for the emergence, a lack of antiviral therapies to treat or prevent this emerging infection are cause for concern. Here we report on the development of a synthetic enhanced DNA vaccine (SEV) against POWV.

In this study, by construct optimization and in vivo electroporation of SEV antigens, the induction of polyfunctional cellular activities and strong neutralizing antibody responses with minimal cross-reactivity against surface antigens of flavivirus endemic to the United States, namely West Nile Virus and Zika virus was observed. An antibody epitope mapping of immune sera spanning the entire envelope regions indicate a pattern similar to that of a convalescent patient serum. Importantly, the POWV-SEV construct induced in vivo protective immunity, as immunized mice were protected from lethal viral challenge, confirming POWV-SEV's capability of providing protection from disease state and mediate the encephalitis-related immunopathology. The results presented herein demonstrate the development and the assessment of a DNA-encoded POWV vaccine that generate potent humoral and cellular immunogenicity. These studies are highly novel, demonstrating that envelope-based POWV DNA vaccine constructs are therapeutic, and provides a new and safe method for POWV vaccine development.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

---

What is claimed:

1. An immunogenic composition comprising a nucleic acid molecule encoding at least one consensus Powassan virus (POWV) antigen, wherein the POWV antigen is selected from the group consisting of a premembrane-envelope (prME) antigen, a capsid antigen, and a combination thereof, and wherein the nucleic acid molecule encodes a peptide comprising an amino acid sequence selected from the group consisting of a) an amino acid sequence having at least 98% identity over the entire length of SEQ ID NO: 10, and b) the amino acid sequence selected from the group consisting of SEQ ID NO: 2, SEQ ID NO: 6 and SEQ ID NO: 10;

wherein the immunogenic composition comprises an adjuvant.

2. The immunogenic composition of claim 1, wherein the nucleic acid molecule is selected from the group consisting of a DNA molecule and an RNA molecule.

3. The immunogenic composition of claim 1, wherein the nucleic acid molecule comprises a nucleotide sequence selected from the group consisting of a) a nucleotide sequence having at least about 95% identity over an entire length of a nucleotide sequence selected from the group consisting of SEQ ID NO: 1, SEQ ID NO: 5 and SEQ ID NO: 9, and b) a nucleotide sequence selected from the group consisting of SEQ ID NO: 1, SEQ ID NO: 5 and SEQ ID NO: 9.

4. The immunogenic composition of claim 1, wherein the nucleotide sequence encoding the peptide is operably linked to at least one regulatory sequence selected from the group consisting of a start codon, an IgE leader sequence and a stop codon.

5. The immunogenic composition of claim 4, wherein the nucleic acid molecule encodes a peptide comprising an amino acid sequence selected from the group consisting of a) an amino acid sequence having at least 98% identity over the entire length of SEQ ID NO: 10, and b) the amino acid sequence selected from the group consisting of SEQ ID NO: 2, SEQ ID NO: 6 and SEQ ID NO: 10, operably linked to an amino acid sequence as set forth in SEQ ID NO: 13.

6. The immunogenic composition of claim 5, wherein the nucleic acid molecule comprises a nucleotide sequence selected from the group consisting of a) a nucleotide sequence having at least about 95% identity over an entire length of a nucleotide sequence selected from the group consisting of SEQ ID NO: 1, SEQ ID NO: 5 and SEQ ID NO: 9, and b) a nucleotide sequence selected from the group consisting of SEQ ID NO: 1, SEQ ID NO: 5 and SEQ ID NO: 9, operably linked to an nucleotide sequence encoding SEQ ID NO: 13.

7. The immunogenic composition of claim 1, wherein the nucleic acid molecule comprises an expression vector.

8. The immunogenic composition of claim 1, wherein the nucleic acid molecule is incorporated into a viral particle.

9. The immunogenic composition of claim 1, further comprising a pharmaceutically acceptable excipient.

10. A method of inducing an immune response against a POWV antigen in a subject in need thereof, the method comprising administering an immunogenic composition of claim 1 to the subject.

11. The method of claim 10, wherein administering includes at least one of electroporation and injection.

12. A method of treating or preventing a POWV associated pathology in subject in need thereof, the method comprising administering an immunogenic composition of claim 1 to the subject.

13. The method of claim 12, wherein administering includes at least one of electroporation and injection.

14. The method of claim 12, wherein the POWV associated pathology is at least one of POWV infection and encephalitis.

15. A peptide comprising an amino acid sequence selected from the group consisting of a) an amino acid sequence having at least 98% identity over the entire length of SEQ ID NO: 10, and b) the amino acid sequence selected from the group consisting of SEQ ID NO: 2, SEQ ID NO: 4, SEQ ID NO: 6, SEQ ID NO: 8, SEQ ID NO: 10 and SEQ ID NO: 12;

wherein the immunogenic composition comprises an adjuvant.

16. An immunogenic composition comprising a peptide of claim 15.

* * * * *

```
                        SEQUENCE LISTING

<160> NUMBER OF SEQ ID NOS: 13

<210> SEQ ID NO 1
<211> LENGTH: 387
<212> TYPE: DNA
<213> ORGANISM: Artificial Sequence
<220> FEATURE:
<223> OTHER INFORMATION: Chemically Synthesized, consensus POWV capsid
      immunogen

<400> SEQUENCE: 1
gtgactacat caaaggggaa gggaggaggg cctcctagga gaaagctgaa ggtgaccgcc         60
aacaagagcc gcccagccac atccccaatg cccaagggct tcgtgctgag caggatgctg        120
ggcatcctgt ggcacgcagt gaccggaaca gccaggcccc ctgtgctgaa gatgttttgg        180
aagaccgtgc cactgagaca ggcagaggcc gccctgaaga agatcaagag agtgatcggc        240
aatctgatgc agtctctgca catgagaggc cggcgcagga gcggagtgga ctggacctgg        300
acattcctga ccatggccct gatgacaatg gcaatggcta caactattca cagagacaga        360
gagggctata tggtcatgcg ggcaagc                                            387

<210> SEQ ID NO 2
<211> LENGTH: 129
<212> TYPE: PRT
<213> ORGANISM: Artificial Sequence
<220> FEATURE:
<223> OTHER INFORMATION: Chemically Synthesized, consensus POWV capsid
      immunogen

<400> SEQUENCE: 2

Val Thr Thr Ser Lys Gly Lys Gly Gly Gly Pro Pro Arg Arg Lys Leu
1               5                   10                  15
```

-continued

```
Lys Val Thr Ala Asn Lys Ser Arg Pro Ala Thr Ser Pro Met Pro Lys
        20                  25                  30

Gly Phe Val Leu Ser Arg Met Leu Gly Ile Leu Trp His Ala Val Thr
        35                  40                  45

Gly Thr Ala Arg Pro Pro Val Leu Lys Met Phe Trp Lys Thr Val Pro
    50                  55                  60

Leu Arg Gln Ala Glu Ala Ala Leu Lys Lys Ile Lys Arg Val Ile Gly
65                  70                  75                  80

Asn Leu Met Gln Ser Leu His Met Arg Gly Arg Arg Ser Gly Val
                85                  90                  95

Asp Trp Thr Trp Thr Phe Leu Thr Met Ala Leu Met Thr Met Ala Met
        100                 105                 110

Ala Thr Thr Ile His Arg Asp Arg Glu Gly Tyr Met Val Met Arg Ala
        115                 120                 125

Ser
```

```
<210> SEQ ID NO 3
<211> LENGTH: 447
<212> TYPE: DNA
<213> ORGANISM: Artificial Sequence
<220> FEATURE:
<223> OTHER INFORMATION: Chemically Synthesized, consensus POWV capsid
      immunogen operably linked to a sequence encoding an IgE leader

<400> SEQUENCE: 3
atggactgga cttggattct gtttctggtc gccgcagcaa cccgcgtgca tagcgtgact      60
acatcaaagg ggaagggagg agggcctcct aggagaaagc tgaaggtgac cgccaacaag     120
agccgcccag ccacatcccc aatgcccaag ggcttcgtgc tgagcaggat gctgggcatc     180
ctgtggcacg cagtgaccgg aacagccagg ccccctgtgc tgaagatgtt ttggaagacc     240
gtgccactga acaggcaga ggccgccctg aagaagatca agagagtgat cggcaatctg     300
atgcagtctc tgcacatgag aggccggcgc aggagcggag tggactggac ctggacattc     360
ctgaccatgg ccctgatgac aatggcaatg gctacaacta ttcacagaga cagagagggc     420
tatatggtca tgcgggcaag ctaatga                                        447
```

```
<210> SEQ ID NO 4
<211> LENGTH: 147
<212> TYPE: PRT
<213> ORGANISM: Artificial Sequence
<220> FEATURE:
<223> OTHER INFORMATION: Chemically Synthesized, consensus POWV capsid
      immunogen operably linked to  an IgE leader

<400> SEQUENCE: 4

Met Asp Trp Thr Trp Ile Leu Phe Leu Val Ala Ala Ala Thr Arg Val
1               5                   10                  15

His Ser Val Thr Thr Ser Lys Gly Lys Gly Gly Gly Pro Pro Arg Arg
        20                  25                  30

Lys Leu Lys Val Thr Ala Asn Lys Ser Arg Pro Ala Thr Ser Pro Met
        35                  40                  45

Pro Lys Gly Phe Val Leu Ser Arg Met Leu Gly Ile Leu Trp His Ala
    50                  55                  60

Val Thr Gly Thr Ala Arg Pro Pro Val Leu Lys Met Phe Trp Lys Thr
65                  70                  75                  80

Val Pro Leu Arg Gln Ala Glu Ala Ala Leu Lys Lys Ile Lys Arg Val
                85                  90                  95
```

```
Ile Gly Asn Leu Met Gln Ser Leu His Met Arg Gly Arg Arg Arg Ser
        100                 105                 110

Gly Val Asp Trp Thr Trp Thr Phe Leu Thr Met Ala Leu Met Thr Met
        115                 120                 125

Ala Met Ala Thr Thr Ile His Arg Asp Arg Glu Gly Tyr Met Val Met
    130                 135                 140

Arg Ala Ser
145
```

<210> SEQ ID NO 5
<211> LENGTH: 1347
<212> TYPE: DNA
<213> ORGANISM: Artificial Sequence
<220> FEATURE:
<223> OTHER INFORMATION: Chemically Synthesized, consensus POWV envelope
      immunogen

<400> SEQUENCE: 5

```
gggagagacg cagcaagtca ggtccgggtg cagaacggca cctgcgtgat cctggccaca      60
gacatgggcg agtggtgcga ggattctatc acctacagct gcgtgacaat cgaccaggag     120
gaggagcccg tggacgtgga ttgcttctgt aggggcgtgg atagagtgaa gctggagtat     180
ggcaggtgtg cagacaggc cggctttcgg ggcaagagga gcgtggtcat ccctacccac     240
gcacagaagg acatggtggg aaggggacac gcatggctga agggcgacaa catccgggat     300 cacgtgacc cgcgtggaggg atggatgtgg aagaataagc tgctgacagt ggccatcgtg     360
gccctggcct ggctgatggt ggactcttgg atggccaggg tgacagtgat cctgctggcc     420
ctgagcctgg acccgtgta cgccacccgg tgcacacacc tggagaaccg cgatttcgtg     480
accggcacac agggcaccac aagagtgtcc ctggtgctgg agctgggcgg ctgcgtgacc     540
atcacagcag agggcaagcc aagcatcgac gtgtggctgg aggatatctt tcaggagtcc     600
cccgccgaga caagggagta ttgcctgcac gccaagctga ccaatacaaa ggtggaggca     660
aggtgtccaa ccacaggacc agccacactg cctgaggagc accaggccaa catggtgtgc     720
aagagggacc agtccgatag aggctggggc aatcactgtg gcttctttgg caagggctct     780
atcgtggcct gcgccaagtt cgagtgtgag gaggccaaga aggccgtggg ccacgtgtac     840
gacagcacca agatcacata tgtggtgaag gtggagccac acaccggcga ttacctggcc     900
gccaacgaga caaactccaa taggaagtct gcccagttta ccgtggcctc cgagaaagtg     960
atcctgagac tgggcgacta tggcgatgtg agcctgacct gcaaggtggc atccggaatc    1020
gacgtggcac agacagtggt catgtccctg ggcagctcca aggatcacct gccttctgcc    1080
tggcaggtgc accgcgactg gttcgaggat ctggccctgc catggaagca caaggacaac    1140
caggattgga atagcgtgga aagctggtg gagttcggcc ctccccacgc agtgaagatg    1200
gacgtgttta atctgggcga tcagaccgcc gtgctgctga gtctctggc aggagtgcca    1260 ctggcaagcg tggagggcca gaagtaccac ctgaaaagcg gcatgtgac ttgcgatgtc    1320 ggactggaaa aactgaaact gaaaggc                                        1347
```

<210> SEQ ID NO 6
<211> LENGTH: 448
<212> TYPE: PRT
<213> ORGANISM: Artificial Sequence
<220> FEATURE:
<223> OTHER INFORMATION: Chemically Synthesized, consensus POWV envelope
      immunogen

```
<400> SEQUENCE: 6

Gly Arg Asp Ala Ala Ser Gln Val Arg Val Gln Asn Gly Thr Cys Val
1               5                   10                  15

Ile Leu Ala Thr Asp Met Gly Glu Trp Cys Glu Asp Ser Ile Thr Tyr
                20                  25                  30

Ser Cys Val Thr Ile Asp Gln Glu Glu Pro Val Asp Val Asp Cys Phe
            35                  40                  45

Cys Arg Gly Val Asp Arg Val Lys Leu Glu Tyr Gly Arg Cys Gly Arg
        50                  55                  60

Gln Ala Gly Phe Arg Gly Lys Arg Ser Val Val Ile Pro Thr His Ala
65                  70                  75                  80

Gln Lys Asp Met Val Gly Arg Gly His Ala Trp Leu Lys Gly Asp Asn
                85                  90                  95

Ile Arg Asp His Val Thr Arg Val Glu Gly Trp Met Trp Lys Asn Lys
            100                 105                 110

Leu Leu Thr Val Ala Ile Val Ala Leu Ala Trp Leu Met Val Asp Ser
            115                 120                 125

Trp Met Ala Arg Val Thr Val Ile Leu Leu Ala Leu Ser Leu Gly Pro
        130                 135                 140

Val Tyr Ala Thr Arg Cys Thr His Leu Glu Asn Arg Asp Phe Val Thr
145                 150                 155                 160

Gly Thr Gln Gly Thr Thr Arg Val Ser Leu Val Leu Glu Leu Gly Gly
                165                 170                 175

Cys Val Thr Ile Thr Ala Glu Gly Lys Pro Ser Ile Asp Val Trp Leu
            180                 185                 190

Glu Asp Ile Phe Gln Glu Ser Pro Ala Glu Thr Arg Glu Tyr Cys Leu
            195                 200                 205

His Ala Lys Leu Thr Asn Thr Lys Val Glu Ala Arg Cys Pro Thr Thr
        210                 215                 220

Gly Pro Ala Thr Leu Pro Glu Glu His Gln Ala Asn Met Val Cys Lys
225                 230                 235                 240

Arg Asp Gln Ser Asp Arg Gly Trp Gly Asn His Cys Gly Phe Phe Gly
                245                 250                 255

Lys Gly Ser Ile Val Ala Cys Ala Lys Phe Glu Cys Glu Glu Ala Lys
            260                 265                 270

Lys Ala Val Gly His Val Tyr Asp Ser Thr Lys Ile Thr Tyr Val Val
        275                 280                 285

Lys Val Glu Pro His Thr Gly Asp Tyr Leu Ala Ala Asn Glu Thr Asn
    290                 295                 300

Ser Asn Arg Lys Ser Ala Gln Phe Thr Val Ala Ser Glu Lys Val Ile
305                 310                 315                 320

Leu Arg Leu Gly Asp Tyr Gly Asp Val Ser Leu Thr Cys Lys Val Ala
                325                 330                 335

Ser Gly Ile Asp Val Ala Gln Thr Val Val Met Ser Leu Gly Ser Ser
            340                 345                 350

Lys Asp His Leu Pro Ser Ala Trp Gln Val His Arg Asp Trp Phe Glu
            355                 360                 365

Asp Leu Ala Leu Pro Trp Lys His Lys Asp Asn Gln Asp Trp Asn Ser
        370                 375                 380

Val Glu Lys Leu Val Glu Phe Gly Pro Pro His Ala Val Lys Met Asp
385                 390                 395                 400

Val Phe Asn Leu Gly Asp Gln Thr Ala Val Leu Leu Lys Ser Leu Ala
                405                 410                 415
```

-continued

```
Gly Val Pro Leu Ala Ser Val Glu Gly Gln Lys Tyr His Leu Lys Ser
        420                 425                 430

Gly His Val Thr Cys Asp Val Gly Leu Glu Lys Leu Lys Leu Lys Gly
        435                 440                 445
```

<210> SEQ ID NO 7
<211> LENGTH: 1407
<212> TYPE: DNA
<213> ORGANISM: Artificial Sequence
<220> FEATURE:
<223> OTHER INFORMATION: Chemically Synthesized, a consensus POWV
      envelope immunogen operably linked to a sequence encoding an IgE
      leader

<400> SEQUENCE: 7

```
atggattgga catggattct gtttctggtc gcagccgcca cacgagtgca ttcagggaga     60
gacgcagcaa gtcaggtccg ggtgcagaac ggcacctgcg tgatcctggc cacagacatg    120
ggcgagtggt gcgaggattc tatcacctac agctgcgtga caatcgacca ggaggaggag    180
cccgtggacg tggattgctt ctgtaggggc gtggatagag tgaagctgga gtatggcagg    240
tgtggcagac aggccggctt tcggggcaag aggagcgtgg tcatccctac ccacgcacag    300
aaggacatgg tgggaagggg acacgcatgg ctgaagggcg acaacatccg ggatcacgtg    360
acccgcgtgg agggatggat gtggaagaat aagctgctga cagtggccat cgtgccctg     420 gcctggctga tggtggactc ttggatggcc agggtgacag tgatcctgct ggccctgagc    480
ctgggacccg tgtacgccac ccggtgcaca cacctggaga ccgcgatttt cgtgaccggc    540
acacagggca ccacaagagt gtccctggtg ctggagctgg cggctgcgt gaccatcaca     600 gcagagggca agccaagcat cgacgtgtgg ctggaggata tctttcagga gtcccccgcc    660
gagacaaggg agtattgcct gcacgccaag ctgaccaata caaaggtgga ggcaaggtgt    720
ccaaccacag gaccagccac actgcctgag gagcaccagg ccaacatggt gtgcaagagg    780
gaccagtccg atagaggctg gggcaatcac tgtggcttct ttggcaaggg ctctatcgtg    840
gcctgcgcca gttcgagtg tgaggaggcc aagaaggccg tgggccacgt gtacgacagc    900
accaagatca catatgtggt gaaggtggag ccacacaccg gcgattacct ggccgccaac    960
gagacaaact ccaataggaa gtctgcccag tttaccgtgg cctccgagaa agtgatcctg   1020
agactgggcg actatggcga tgtgagcctg acctgcaagg tggcatccgg aatcgacgtg   1080
gcacagacag tggtcatgtc cctgggcagc tccaaggatc acctgccttc tgcctggcag   1140
gtgcaccgcg actggttcga ggatctggcc ctgccatgag agcacaagga caaccaggat   1200
tggaatagcg tggagaagct ggtggagttc ggccctcccc acgcagtgaa gatggacgtg   1260
tttaatctgg gcgatcagac cgccgtgctg ctgaagtctc tggcaggagt gccactggca   1320
agcgtggagg ccagaagta ccacctgaaa agcgggcatg tgacttgcga tgtcggactg   1380
gaaaaactga aactgaaagg ctaatga                                       1407
```

<210> SEQ ID NO 8
<211> LENGTH: 466
<212> TYPE: PRT
<213> ORGANISM: Artificial Sequence
<220> FEATURE:
<223> OTHER INFORMATION: Chemically Synthesized, a consensus POWV
      envelope immunogen operably linked to an IgE leader

<400> SEQUENCE: 8

```
Met Asp Trp Thr Trp Ile Leu Phe Leu Val Ala Ala Ala Thr Arg Val
```

-continued

```
1                    5                    10                    15

His Ser Gly Arg Asp Ala Ala Ser Gln Val Arg Val Gln Asn Gly Thr
            20                    25                    30

Cys Val Ile Leu Ala Thr Asp Met Gly Glu Trp Cys Glu Asp Ser Ile
            35                    40                    45

Thr Tyr Ser Cys Val Thr Ile Asp Gln Glu Glu Pro Val Asp Val Asp
        50                    55                    60

Cys Phe Cys Arg Gly Val Asp Arg Val Lys Leu Glu Tyr Gly Arg Cys
65                    70                    75                    80

Gly Arg Gln Ala Gly Phe Arg Gly Lys Arg Ser Val Val Ile Pro Thr
                85                    90                    95

His Ala Gln Lys Asp Met Val Gly Arg Gly His Ala Trp Leu Lys Gly
            100                   105                   110

Asp Asn Ile Arg Asp His Val Thr Arg Val Glu Gly Trp Met Trp Lys
            115                   120                   125

Asn Lys Leu Leu Thr Val Ala Ile Val Ala Leu Ala Trp Leu Met Val
        130                   135                   140

Asp Ser Trp Met Ala Arg Val Thr Val Ile Leu Leu Ala Leu Ser Leu
145                   150                   155                   160

Gly Pro Val Tyr Ala Thr Arg Cys Thr His Leu Glu Asn Arg Asp Phe
                165                   170                   175

Val Thr Gly Thr Gln Gly Thr Thr Arg Val Ser Leu Val Leu Glu Leu
            180                   185                   190

Gly Gly Cys Val Thr Ile Thr Ala Glu Gly Lys Pro Ser Ile Asp Val
            195                   200                   205

Trp Leu Glu Asp Ile Phe Gln Glu Ser Pro Ala Glu Thr Arg Glu Tyr
        210                   215                   220

Cys Leu His Ala Lys Leu Thr Asn Thr Lys Val Glu Ala Arg Cys Pro
225                   230                   235                   240

Thr Thr Gly Pro Ala Thr Leu Pro Glu Glu His Gln Ala Asn Met Val
                245                   250                   255

Cys Lys Arg Asp Gln Ser Asp Arg Gly Trp Gly Asn His Cys Gly Phe
            260                   265                   270

Phe Gly Lys Gly Ser Ile Val Ala Cys Ala Lys Phe Glu Cys Glu Glu
        275                   280                   285

Ala Lys Lys Ala Val Gly His Val Tyr Asp Ser Thr Lys Ile Thr Tyr
        290                   295                   300

Val Val Lys Val Glu Pro His Thr Gly Asp Tyr Leu Ala Ala Asn Glu
305                   310                   315                   320

Thr Asn Ser Asn Arg Lys Ser Ala Gln Phe Thr Val Ala Ser Glu Lys
                325                   330                   335

Val Ile Leu Arg Leu Gly Asp Tyr Gly Asp Val Ser Leu Thr Cys Lys
            340                   345                   350

Val Ala Ser Gly Ile Asp Val Ala Gln Thr Val Val Met Ser Leu Gly
        355                   360                   365

Ser Ser Lys Asp His Leu Pro Ser Ala Trp Gln Val His Arg Asp Trp
        370                   375                   380

Phe Glu Asp Leu Ala Leu Pro Trp Lys His Lys Asp Asn Gln Asp Trp
385                   390                   395                   400

Asn Ser Val Glu Lys Leu Val Glu Phe Gly Pro Pro His Ala Val Lys
                405                   410                   415

Met Asp Val Phe Asn Leu Gly Asp Gln Thr Ala Val Leu Leu Lys Ser
            420                   425                   430
```

```
Leu Ala Gly Val Pro Leu Ala Ser Val Glu Gly Gln Lys Tyr His Leu
        435                 440                 445

Lys Ser Gly His Val Thr Cys Asp Val Gly Leu Glu Lys Leu Lys Leu
    450                 455                 460

Lys Gly
465

<210> SEQ ID NO 9
<211> LENGTH: 1761
<212> TYPE: DNA
<213> ORGANISM: Artificial Sequence
<220> FEATURE:
<223> OTHER INFORMATION: Chemically Synthesized, consensus POWV capsid
      and envelope immunogen

<400> SEQUENCE: 9
gtgactactt caaaaggcaa aggaggaggc ccccccagga gaaagctgaa ggtgaccgcc        60
aacaagagcc gccctgccac atcccctatg ccaaagggct tcgtgctgag caggatgctg       120
ggcatcctgt ggcacgcagt gaccggaaca gccagacccc ctgtgctgaa gatgttttgg       180
aagaccgtgc ctctgagaca ggcagaggcc gccctgaaga agatcaagag agtgatcggc       240
aatctgatgc agtctctgca catgaggggc cggcgcagga gcggagtgga ctggacctgg       300
acattcctga ccatggccct gatgacaatg gccatggcca ccacaatcca ccgcgatagg       360
gagggctaca tggtcatgag agcctctaga ggcaggaaga acggagcgc caccggaaga       420 gacgcagcat ctcaggtgcg ggtgcagaac ggcacctgcg tgatcctggc cacagacatg       480
ggcgagtggt gcgaggattc tatcacctac agctgcgtga caatcgacca ggaggaggag       540
cccgtggacg tggattgctt ctgtcgcggc gtggataggg tgaagctgga gtatggccgc       600
tgtggcaggc aggcaggctt tagaggcaag cggagcgtgg tcatccctac ccacgcacag       660
aaggacatgg tgggaagggg acacgcatgg ctgaagggcg acaacatcag agatcacgtg       720
acccgggtgg agggctggat gtggaagaat aagctgctga cagtggccat cgtggccctg       780
gcctggctga tggtggattc ttggatggcc cgggtgacag tgatcctgct ggccctgagc       840
ctgggacccg tgtacgccac ccgctgcaca cacctggaga cagggactt cgtgaccgga       900 acacagggaa ccacacgcgt gtccctggtg ctggagctgg cggctgcgt gaccatcaca       960 gcagagggca agccaagcat cgacgtgtgg ctggaggata tctttcagga gtcccccgcc      1020
gagacaaggg agtattgcct gcacgccaag ctgaccaata caaaggtgga ggccagatgt      1080
cccaccacag gccctgccac actgccagag gagcaccagg ccaacatggt gtgcaagcgc      1140
gaccagtccg atagggctg gggcaatcac tgtggcttct ttggcaaggg ctctatcgtg      1200
gcctgcgcca gttcgagtg tgaggaggcc aagaaggccg tgggccacgt gtacgacagc      1260
accaagatca catatgtggt gaaggtggag ccacacaccg gcgattacct ggccgccaac      1320
gagacaaact ccaatcggaa gtctgcccag tttaccgtgg cctccagaa agtgatcctg      1380 cgcctgggcg actatggcga cgtgagcctg acctgcaagg tggcctctgg catcgacgtg      1440
gcccagacag tggtcatgtc cctgggcagc tccaaggatc acctgccttc tgcctggcag      1500
gtgcaccgcg actggtttga ggatctggcc ctgccatgaa gcacaagga caaccaggat      1560 tggaattctg tggagaagct ggtggagttc ggcccacccc acgcagtgaa gatggacgtg      1620
tttaatctgg cgatcagac cgccgtgctg ctgaagagcc tggcaggagt gccactggca      1680
tccgtggagg gccagaagta tcacctgaaa agcgggcatg tgacctgcga tgtggggctg      1740
```
gaaaaactga aactgaaagg g                                                                    1761

<210> SEQ ID NO 10
<211> LENGTH: 587
<212> TYPE: PRT
<213> ORGANISM: Artificial Sequence
<220> FEATURE:
<223> OTHER INFORMATION: Chemically Synthesized, consensus POWV capsid
      and envelope immunogen

<400> SEQUENCE: 10

Val Thr Thr Ser Lys Gly Lys Gly Gly Pro Pro Arg Arg Lys Leu
1               5                   10                  15

Lys Val Thr Ala Asn Lys Ser Arg Pro Ala Thr Ser Pro Met Pro Lys
            20                  25                  30

Gly Phe Val Leu Ser Arg Met Leu Gly Ile Leu Trp His Ala Val Thr
            35                  40                  45

Gly Thr Ala Arg Pro Pro Val Leu Lys Met Phe Trp Lys Thr Val Pro
        50                  55                  60

Leu Arg Gln Ala Glu Ala Ala Leu Lys Lys Ile Lys Arg Val Ile Gly
65                  70                  75                  80

Asn Leu Met Gln Ser Leu His Met Arg Gly Arg Arg Arg Ser Gly Val
                85                  90                  95

Asp Trp Thr Trp Thr Phe Leu Thr Met Ala Leu Met Thr Met Ala Met
                100                 105                 110

Ala Thr Thr Ile His Arg Asp Arg Glu Gly Tyr Met Val Met Arg Ala
            115                 120                 125

Ser Arg Gly Arg Lys Arg Arg Ser Ala Thr Gly Arg Asp Ala Ala Ser
            130                 135                 140

Gln Val Arg Val Gln Asn Gly Thr Cys Val Ile Leu Ala Thr Asp Met
145                 150                 155                 160

Gly Glu Trp Cys Glu Asp Ser Ile Thr Tyr Ser Cys Val Thr Ile Asp
                165                 170                 175

Gln Glu Glu Glu Pro Val Asp Val Asp Cys Phe Cys Arg Gly Val Asp
                180                 185                 190

Arg Val Lys Leu Glu Tyr Gly Arg Cys Gly Arg Gln Ala Gly Phe Arg
            195                 200                 205

Gly Lys Arg Ser Val Val Ile Pro Thr His Ala Gln Lys Asp Met Val
            210                 215                 220

Gly Arg Gly His Ala Trp Leu Lys Gly Asp Asn Ile Arg Asp His Val
225                 230                 235                 240

Thr Arg Val Glu Gly Trp Met Trp Lys Asn Lys Leu Leu Thr Val Ala
                245                 250                 255

Ile Val Ala Leu Ala Trp Leu Met Val Asp Ser Trp Met Ala Arg Val
            260                 265                 270

Thr Val Ile Leu Leu Ala Leu Ser Leu Gly Pro Val Tyr Ala Thr Arg
            275                 280                 285

Cys Thr His Leu Glu Asn Arg Asp Phe Val Thr Gly Thr Gln Gly Thr
            290                 295                 300

Thr Arg Val Ser Leu Val Leu Glu Leu Gly Gly Cys Val Thr Ile Thr
305                 310                 315                 320

Ala Glu Gly Lys Pro Ser Ile Asp Val Trp Leu Glu Asp Ile Phe Gln
                325                 330                 335

Glu Ser Pro Ala Glu Thr Arg Glu Tyr Cys Leu His Ala Lys Leu Thr
            340                 345                 350

-continued

```
Asn Thr Lys Val Glu Ala Arg Cys Pro Thr Thr Gly Pro Ala Thr Leu
        355                 360             365

Pro Glu Glu His Gln Ala Asn Met Val Cys Lys Arg Asp Gln Ser Asp
    370                 375             380

Arg Gly Trp Gly Asn His Cys Gly Phe Phe Gly Lys Gly Ser Ile Val
385                 390             395                 400

Ala Cys Ala Lys Phe Glu Cys Glu Glu Ala Lys Lys Ala Val Gly His
                405             410             415

Val Tyr Asp Ser Thr Lys Ile Thr Tyr Val Val Lys Val Glu Pro His
            420             425             430

Thr Gly Asp Tyr Leu Ala Ala Asn Glu Thr Asn Ser Asn Arg Lys Ser
            435             440             445

Ala Gln Phe Thr Val Ala Ser Glu Lys Val Ile Leu Arg Leu Gly Asp
    450             455             460

Tyr Gly Asp Val Ser Leu Thr Cys Lys Val Ala Ser Gly Ile Asp Val
465             470             475             480

Ala Gln Thr Val Val Met Ser Leu Gly Ser Ser Lys Asp His Leu Pro
            485             490             495

Ser Ala Trp Gln Val His Arg Asp Trp Phe Glu Asp Leu Ala Leu Pro
        500             505             510

Trp Lys His Lys Asp Asn Gln Asp Trp Asn Ser Val Glu Lys Leu Val
        515             520             525

Glu Phe Gly Pro Pro His Ala Val Lys Met Asp Val Phe Asn Leu Gly
    530             535             540

Asp Gln Thr Ala Val Leu Leu Lys Ser Leu Ala Gly Val Pro Leu Ala
545             550             555             560

Ser Val Glu Gly Gln Lys Tyr His Leu Lys Ser Gly His Val Thr Cys
            565             570             575

Asp Val Gly Leu Glu Lys Leu Lys Leu Lys Gly
            580             585
```

<210> SEQ ID NO 11
<211> LENGTH: 1821
<212> TYPE: DNA
<213> ORGANISM: Artificial Sequence
<220> FEATURE:
<223> OTHER INFORMATION: Chemically Synthesized, consensus POWV capsid
      and envelope immunogen operably linked to a sequence encoding an
      IgE leader

<400> SEQUENCE: 11

```
atggattgga cttggattct gtttctggtc gcagccgcaa ctcgcgtgca tagcgtgact      60
acttcaaaag gcaaaggagg aggcccccc aggagaaagc tgaaggtgac cgccaacaag     120
agccgccctg ccacatcccc tatgccaaag ggcttcgtgc tgagcaggat gctgggcatc     180
ctgtggcacg cagtgaccgg aacagccaga cccctgtgc tgaagatgtt ttggaagacc     240
gtgcctctga acaggcaga ggccgccctg aagaagatca agagagtgat cggcaatctg     300
atgcagtctc tgcacatgag gggccggcgc aggagcggag tggactggac ctggacattc     360
ctgaccatgg ccctgatgac aatggccatg gccaccacaa tccaccgcga tagggagggc     420
tacatggtca tgagagcctc tagaggcagg aagagacgga gcgccaccgg aagagacgca     480
gcatctcagg tgcgggtgca gaacggcacc tgcgtgatcc tggccacaga catgggcgag     540
tggtgcgagg attctatcac ctacagctgc gtgacaatcg accaggagga ggagcccgtg     600
gacgtggatt gcttctgtcg cggcgtggat agggtgaagc tggagtatgg ccgctgtggc     660
```

-continued

```
aggcaggcag gctttagagg caagcggagc gtggtcatcc ctacccacgc acagaaggac      720
atggtgggaa ggggacacgc atggctgaag ggcgacaaca tcagagatca cgtgacccgg      780
gtggagggct ggatgtggaa gaataagctg ctgacagtgg ccatcgtggc cctggcctgg      840
ctgatggtgg attcttggat ggcccgggtg acagtgatcc tgctggccct gagcctggga      900
cccgtgtacg ccacccgctg cacacacctg gagaacaggg acttcgtgac cggaacacag      960
ggaaccacac gcgtgtccct ggtgctggag ctgggcggct gcgtgaccat cacagcagag     1020
ggcaagccaa gcatcgacgt gtggctggag gatatctttc aggagtcccc cgccgagaca     1080
agggagtatt gcctgcacgc caagctgacc aatacaaagg tggaggccag atgtcccacc     1140
acaggccctg ccacactgcc agaggagcac caggccaaca tggtgtgcaa gcgcgaccag     1200
tccgataggg gctggggcaa tcactgtggc ttctttggca agggctctat cgtggcctgc     1260
gccaagttcg agtgtgagga ggccaagaag gccgtgggcc acgtgtacga cagcaccaag     1320
atcacatatg tggtgaaggt ggagccacac accggcgatt acctggccgc caacgagaca     1380
aactccaatc ggaagtctgc ccagtttacc gtggcctccg agaaagtgat cctgcgcctg     1440
ggcgactatg cgacgtgag cctgacctgc aaggtggcct ctggcatcga cgtggcccag     1500
acagtggtca tgtccctggg cagctccaag gatcacctgc cttctgcctg caggtgcac     1560 cgcgactggt ttgaggatct ggccctgcca tggaagcaca aggacaacca ggattggaat     1620
tctgtggaga agctggtgga gttcggccca ccccacgcag tgaagatgga cgtgtttaat     1680
ctgggcgatc agaccgccgt gctgctgaag agcctggcag gagtgccact ggcatccgtg     1740
gagggccaga agtatcacct gaaaagcggg catgtgacct cgatgtggg gctggaaaaa     1800 ctgaaactga aagggtaatg a                                             1821
```

<210> SEQ ID NO 12
<211> LENGTH: 605
<212> TYPE: PRT
<213> ORGANISM: Artificial Sequence
<220> FEATURE:
<223> OTHER INFORMATION: Chemically Synthesized, consensus POWV capsid
      and envelope immunogen operably linked to an IgE leader

<400> SEQUENCE: 12

```
Met Asp Trp Thr Trp Ile Leu Phe Leu Val Ala Ala Ala Thr Arg Val
1               5                   10                  15

His Ser Val Thr Thr Ser Lys Gly Lys Gly Gly Pro Pro Arg Arg
            20                  25                  30

Lys Leu Lys Val Thr Ala Asn Lys Ser Arg Pro Ala Thr Ser Pro Met
        35                  40                  45

Pro Lys Gly Phe Val Leu Ser Arg Met Leu Gly Ile Leu Trp His Ala
    50                  55                  60

Val Thr Gly Thr Ala Arg Pro Pro Val Leu Lys Met Phe Trp Lys Thr
65                  70                  75                  80

Val Pro Leu Arg Gln Ala Glu Ala Ala Leu Lys Lys Ile Lys Arg Val
                85                  90                  95

Ile Gly Asn Leu Met Gln Ser Leu His Met Arg Gly Arg Arg Ser
            100                 105                 110

Gly Val Asp Trp Thr Trp Thr Phe Leu Thr Met Ala Leu Met Thr Met
        115                 120                 125

Ala Met Ala Thr Thr Ile His Arg Asp Arg Glu Gly Tyr Met Val Met
    130                 135                 140

Arg Ala Ser Arg Gly Arg Lys Arg Arg Ser Ala Thr Gly Arg Asp Ala
```

-continued

```
145               150               155               160

Ala Ser Gln Val Arg Val Gln Asn Gly Thr Cys Val Ile Leu Ala Thr
                165               170               175

Asp Met Gly Glu Trp Cys Glu Asp Ser Ile Thr Tyr Ser Cys Val Thr
                180               185               190

Ile Asp Gln Glu Glu Glu Pro Val Asp Val Asp Cys Phe Cys Arg Gly
                195               200               205

Val Asp Arg Val Lys Leu Glu Tyr Gly Arg Cys Gly Arg Gln Ala Gly
        210               215               220

Phe Arg Gly Lys Arg Ser Val Val Ile Pro Thr His Ala Gln Lys Asp
225               230               235               240

Met Val Gly Arg Gly His Ala Trp Leu Lys Gly Asp Asn Ile Arg Asp
                245               250               255

His Val Thr Arg Val Glu Gly Trp Met Trp Lys Asn Lys Leu Leu Thr
                260               265               270

Val Ala Ile Val Ala Leu Ala Trp Leu Met Val Asp Ser Trp Met Ala
                275               280               285

Arg Val Thr Val Ile Leu Leu Ala Leu Ser Leu Gly Pro Val Tyr Ala
        290               295               300

Thr Arg Cys Thr His Leu Glu Asn Arg Asp Phe Val Thr Gly Thr Gln
305               310               315               320

Gly Thr Thr Arg Val Ser Leu Val Leu Glu Leu Gly Gly Cys Val Thr
                325               330               335

Ile Thr Ala Glu Gly Lys Pro Ser Ile Asp Val Trp Leu Glu Asp Ile
                340               345               350

Phe Gln Glu Ser Pro Ala Glu Thr Arg Glu Tyr Cys Leu His Ala Lys
                355               360               365

Leu Thr Asn Thr Lys Val Glu Ala Arg Cys Pro Thr Thr Gly Pro Ala
        370               375               380

Thr Leu Pro Glu Glu His Gln Ala Asn Met Val Cys Lys Arg Asp Gln
385               390               395               400

Ser Asp Arg Gly Trp Gly Asn His Cys Gly Phe Phe Gly Lys Gly Ser
                405               410               415

Ile Val Ala Cys Ala Lys Phe Glu Cys Glu Glu Ala Lys Lys Ala Val
                420               425               430

Gly His Val Tyr Asp Ser Thr Lys Ile Thr Tyr Val Val Lys Val Glu
        435               440               445

Pro His Thr Gly Asp Tyr Leu Ala Ala Asn Glu Thr Asn Ser Asn Arg
        450               455               460

Lys Ser Ala Gln Phe Thr Val Ala Ser Glu Lys Val Ile Leu Arg Leu
465               470               475               480

Gly Asp Tyr Gly Asp Val Ser Leu Thr Cys Lys Val Ala Ser Gly Ile
                485               490               495

Asp Val Ala Gln Thr Val Val Met Ser Leu Gly Ser Ser Lys Asp His
        500               505               510

Leu Pro Ser Ala Trp Gln Val His Arg Asp Trp Phe Glu Asp Leu Ala
        515               520               525

Leu Pro Trp Lys His Lys Asp Asn Gln Asp Trp Asn Ser Val Glu Lys
        530               535               540

Leu Val Glu Phe Gly Pro Pro His Ala Val Lys Met Asp Val Phe Asn
545               550               555               560

Leu Gly Asp Gln Thr Ala Val Leu Leu Lys Ser Leu Ala Gly Val Pro
                565               570               575
```

-continued

```
Leu Ala Ser Val Glu Gly Gln Lys Tyr His Leu Lys Ser Gly His Val
            580                 585                 590

Thr Cys Asp Val Gly Leu Glu Lys Leu Lys Leu Lys Gly
        595                 600                 605

<210> SEQ ID NO 13
<211> LENGTH: 18
<212> TYPE: PRT
<213> ORGANISM: Artificial Sequence
<220> FEATURE:
<223> OTHER INFORMATION: Chemically Synthesized, IgE leader sequence

<400> SEQUENCE: 13

Met Asp Trp Thr Trp Ile Leu Phe Leu Val Ala Ala Ala Thr Arg Val
1               5                   10                  15

His Ser
```